United States Patent
Wu et al.

(10) Patent No.: US 9,846,136 B2
(45) Date of Patent: Dec. 19, 2017

(54) MULTI-REGION AND POTENTIAL TEST SENSORS, METHODS AND SYSTEMS

(75) Inventors: Huan-Ping Wu, Granger, IN (US);
Weiping Zhong, Granger, IN (US);
Joseph E. Perry, Osceola, IN (US);
Eric Maurer, Troy, OH (US);
Sung-Kwon Jung, Rensselaer, IN (US)

(73) Assignee: Ascensia Diabetes Care Holdings AG, Basel (CH)

( * ) Notice: Subject to any disclaimer, the term of this patent is extended or adjusted under 35 U.S.C. 154(b) by 602 days.

(21) Appl. No.: 12/728,457

(22) Filed: Mar. 22, 2010

(65) Prior Publication Data
US 2010/0267161 A1    Oct. 21, 2010

Related U.S. Application Data

(63) Continuation of application No. PCT/US2008/077434, filed on Sep. 24, 2008.

(60) Provisional application No. 60/974,823, filed on Sep. 24, 2007.

(51) Int. Cl.
*G01N 27/00* (2006.01)
*G01N 27/327* (2006.01)
*C12Q 1/00* (2006.01)

(52) U.S. Cl.
CPC .......... *G01N 27/3272* (2013.01); *C12Q 1/001* (2013.01); *G01N 27/3274* (2013.01)

(58) Field of Classification Search
CPC . C12Q 1/001; G01N 27/3272; G01N 27/3274
USPC ........................................ 436/149; 422/82.01
See application file for complete search history.

(56) References Cited

U.S. PATENT DOCUMENTS

| | | |
|---|---|---|
| 5,120,420 A | 6/1992 | Nankai et al. |
| 5,393,615 A | 2/1995 | Cory et al. |
| 5,498,542 A | 3/1996 | Cory et al. |
| 5,520,786 A | 5/1996 | Bloczynski et al. |
| 5,620,579 A | 4/1997 | Genshaw et al. |
| 5,653,863 A | 8/1997 | Genshaw et al. |

(Continued)

FOREIGN PATENT DOCUMENTS

| | | |
|---|---|---|
| DE | 202005020335 | 5/2006 |
| EP | 1029928 | 9/2002 |

(Continued)

OTHER PUBLICATIONS

International Searching Authority, "International Search Report and Written Opinion for PCT/US2008/077434", dated Apr. 6, 2009, Publisher: European Patent Office, Published in: EP.

(Continued)

*Primary Examiner* — Rebecca M Fritchman
(74) *Attorney, Agent, or Firm* — Nixon Peabody LLP

(57) ABSTRACT

Biosensor systems including a measurement device and test sensors including at least three independently addressable electrodes, with at least two of the electrodes being substantially chemically isolated are disclosed. One or more working electrodes may be combined with two or more counter electrodes. The two or more counter electrodes may operate at different potentials to provide for multi-analyte electrochemical analysis. Analysis methods are provided to perform multi-analyte electrochemical analysis and test sensors are provided having resistance to chemical mixing between secondary analysis regions.

36 Claims, 23 Drawing Sheets

(56) References Cited

U.S. PATENT DOCUMENTS

| | | |
|---|---|---|
| 5,807,375 A | 9/1998 | Gross et al. |
| 5,906,921 A | 5/1999 | Ikeda et al. |
| 6,120,676 A | 9/2000 | Heller et al. |
| 6,153,069 A | 11/2000 | Pottgen et al. |
| 6,275,717 B1 | 8/2001 | Gross et al. |
| 6,413,411 B1 | 7/2002 | Pottgen et al. |
| 6,824,670 B2 | 11/2004 | Tokunaga et al. |
| 6,984,307 B2 | 1/2006 | Zweig |
| 7,122,111 B2 | 10/2006 | Tokunaga et al. |
| 7,351,323 B2 | 4/2008 | Iketaki et al. |
| 7,749,766 B2 | 7/2010 | Pei et al. |
| 7,785,271 B2 | 8/2010 | Masaki et al. |
| 7,955,492 B2 | 6/2011 | Fujiwara et al. |
| 2002/0127736 A1* | 9/2002 | Chou et al. ............ 436/180 |
| 2004/0040866 A1* | 3/2004 | Miyashita ............ C12Q 1/004 205/777.5 |
| 2005/0109618 A1 | 5/2005 | Davies |
| 2005/0123443 A1* | 6/2005 | Fujiwara ............ A61B 5/157 422/400 |
| 2005/0196747 A1 | 9/2005 | Stiene |
| 2006/0195157 A1* | 8/2006 | Lee et al. ............ 607/46 |
| 2007/0014695 A1 | 1/2007 | Yue et al. |
| 2007/0062822 A1 | 3/2007 | Fujiwara et al. |
| 2007/0080073 A1 | 4/2007 | Wu et al. |
| 2007/0131565 A1 | 6/2007 | Fujiwara et al. |
| 2007/0202606 A1 | 8/2007 | Noble |
| 2009/0178935 A1* | 7/2009 | Reymond et al. ......... 205/777.5 |

FOREIGN PATENT DOCUMENTS

| | | |
|---|---|---|
| EP | 1707953 | 4/2006 |
| EP | 1729122 | 12/2006 |
| EP | 1742045 | 1/2007 |
| JP | 04160354 | 6/1992 |
| JP | 04264246 | 9/1992 |
| RU | 2271536 | 3/2006 |
| WO | 1996014026 | 10/1995 |
| WO | 2005040407 | 5/2005 |
| WO | 2005054839 | 6/2005 |
| WO | 2005054840 | 6/2005 |
| WO | 2005078118 | 8/2005 |
| WO | 2006015615 | 2/2006 |
| WO | 2007013915 | 2/2007 |
| WO | 2007040913 | 4/2007 |
| WO | 2008044530 | 4/2008 |
| WO | 2008047843 | 4/2008 |

OTHER PUBLICATIONS

Extended European Search Report for European Application No. EP 17 15 8596 dated Jun. Mar. 22, 2017 (7 pages).

* cited by examiner

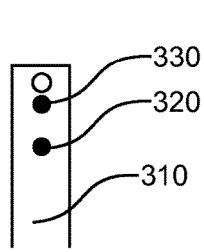 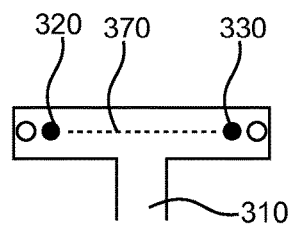 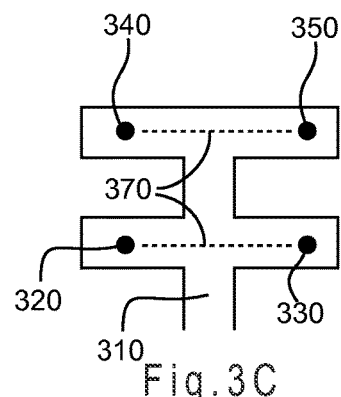
Fig.3A  Fig.3B  Fig.3C
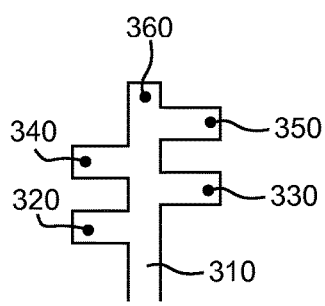 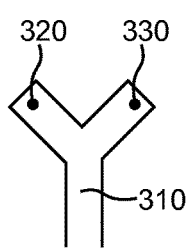 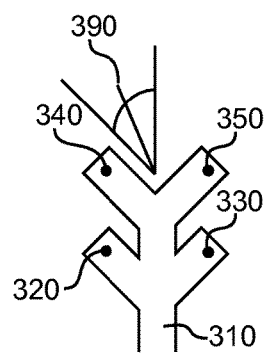
Fig.3D  Fig.3E  Fig.3F
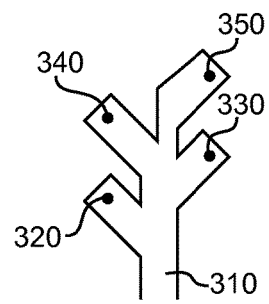
Fig.3G

MULTI-REGION AND POTENTIAL TEST SENSORS, METHODS AND SYSTEMS

REFERENCE TO RELATED APPLICATIONS

This application is a continuation of PCT/US2008/077434 Entitled "Multi-Region and Potential Test Sensors, Methods and Systems" filed Sep. 24, 2008, which was published in English and claimed the benefit of U.S. Provisional Application No. 60/974,823 entitled "Multi-Potential Biosensors, Systems, and Methods" filed Sep. 24, 2007, which are incorporated by reference in their entirety.

BACKGROUND

Biosensors provide an analysis of a biological fluid, such as whole blood, serum, plasma, urine, saliva, interstitial, or intracellular fluid. Typically, biosensors have a measurement device that analyzes a sample residing in a test sensor. The sample is typically in liquid form and in addition to being a biological fluid, may be the derivative of a biological fluid, such as an extract, a dilution, a filtrate, or a reconstituted precipitate. The analysis performed by the biosensor determines the presence and/or concentration of one or more analytes, such as alcohol, glucose, uric acid, lactate, cholesterol, bilirubin, free fatty acids, triglycerides, proteins, ketones, phenylalanine or enzymes, in the biological fluid. The analysis may be useful in the diagnosis and treatment of physiological abnormalities. For example, a diabetic individual may use a biosensor to determine the glucose level in whole blood for adjustments to diet and/or medication.

Many biosensors analyze for a single analyte and use various techniques to improve the accuracy and/or precision of the analysis. Accuracy may be expressed in terms of bias of the sensor system's analyte reading in comparison to a reference analyte reading, with larger bias values representing less accuracy, while precision may be expressed in terms of the spread or variance among multiple measurements. Calibration information may be used to improve the accuracy and/or precision of the analysis and may be read from the test sensor to the measurement device prior to the analysis. The measurement device uses the calibration information to adjust the analysis of the biological fluid in response to one or more parameters, such as the type of biological fluid, the particular analyte(s), and the manufacturing variations of the test sensor. Biosensors may be implemented using bench-top, portable, and like measurement devices. Portable measurement devices may be hand-held and allow for the identification and/or quantification of an analyte in a sample. Examples of portable measurement systems include the Ascensia Breeze® and Elite® meters of Bayer HealthCare in Tarrytown, N.Y., while examples of bench-top measurement systems include the Electrochemical Workstation available from CH Instruments in Austin, Tex.

The electrical signal input to the test sensor by the measurement device may be a potential or current and may be constant, variable, or a combination thereof, such as when an AC signal is applied with a DC signal offset. The input signal may be applied as a single pulse or in multiple pulses, sequences, or cycles. The analyte or a measurable species undergoes a redox reaction when the input signal is applied to the sample. The redox reaction generates the output signal that may be measured constantly or periodically during transient and/or steady-state output. Unlike a transient output signal that is changing, steady-state output is observed when the change of a signal with respect to its independent input variable (time, etc.) is substantially constant, such as within ±10 or ±5%.

Various electrochemical processes may be used such as coulometry, amperometry, voltammetry, or the like. Unlike coulometry, amperometry and voltammetry generally measure the rate at which the analyte is oxidized or reduced to determine the analyte concentration in the sample. In amperometry, an electrical signal of constant potential (voltage) is applied to the electrical conductors of the test sensor while the measured output signal is a current. In voltammetry, a varying potential is applied to a sample of biological fluid. Gated amperometry and gated voltammetry methods including alternating excitation and relaxation cycles also may be used.

The "hematocrit effect" is one factor that may reduce the accuracy and/or precision of an analysis performed in a whole blood sample. In addition to water, glucose, proteins, ketones, and other biological molecules, whole blood samples contain red blood cells. Hematocrit is the volume of a whole blood sample occupied by red blood cells in relation to the total volume of the whole blood sample and is often expressed as a percentage. The greater the hematocrit percentage deviates from the %-hematocrit system calibration for a whole blood sample, the greater the bias (error) in the analyte readings obtained from the biosensor. For example, a conventional biosensor system having one set of calibration constants (slope and intercept for the 40% hematocrit containing whole blood sample, for instance) will report three different glucose concentrations for whole blood samples having identical glucose concentrations, but hematocrit percentages of 20%, 40%, and 60%. Thus, even though the whole blood glucose concentrations are the same, the system will report that the 20% hematocrit whole blood sample contains more glucose than the 40% hematocrit whole blood sample, and that the 60% hematocrit whole blood sample contains less glucose than the 40% hematocrit whole blood sample. As conventional biosensors are generally configured to report glucose concentrations assuming a 40% hematocrit content for the whole blood sample, any glucose measurement performed on a blood sample containing less or more than 40% hematocrit will include some bias error attributable to the hematocrit effect.

Hematocrit bias may be expressed by the following equation:

$$\% \, Hct\text{-Bias} = 100\% \times (G_m - G_{ref})/G_{ref}$$

where $G_m$ and $G_{ref}$ are the measured glucose and reference glucose readings, respectively, for any hematocrit level. The larger the absolute value of the %-Hct-bias, the larger the hematocrit effect.

In addition to the hematocrit effect, measurement inaccuracies also may arise when the measurable species concentration does not correlate with the analyte concentration. For example, when the biosensor determines the concentration of a reduced mediator generated in response to the oxidation of an analyte, any reduced mediator not generated by oxidation of the analyte will lead to an indication that more analyte is present in the sample than is correct due to mediator background.

By knowing the output signal attributable to factors not responsive to the concentration of the analyte, the spurious portion of the output signal may be subtracted. Conventional systems have attempted to isolate the non-responsive portions of the output signal by placing multiples pairs of working and counter electrodes in a common sample reservoir. By altering the reagents used to form the electrodes, these systems attempted to separate the analyte responsive and non-responsive portions by subtracting the two output signals.

For example, conventional sensor systems may have multiple detection areas in an undivided sample chamber, where each working electrode faces a reference electrode. In another aspect, these systems may have a single reference electrode. Systems of these types may provide an on-test sensor calibration system with two known standards or may provide separate electrode systems for analyte, interference, and hematocrit determination, for example. A disadvantage common to these systems is the single sample chamber, where the adjacent electrode systems/detection areas may be contaminated chemically from each other due to diffusion and/or liquid movement. This disadvantage may be especially problematic when one reagent system requires a longer assay time than another and/or when the test sensor is mechanically disturbed after filling with sample.

As more and more information regarding the analytes present in biological samples is necessary for diagnosis, there is an increasing need for routine monitoring of multiple biological species of medical importance. Accordingly, there is an ongoing need for improved biosensors, especially those that may provide increasingly accurate and/or precise concentration measurements for multiple analytes. The systems, devices, and methods of the present invention avoid or ameliorate at least one of the disadvantages associated with conventional biosensors.

SUMMARY

An analyte test sensor is disclosed that includes at least two substrates forming a reservoir, the reservoir having at least two substantially chemically isolated secondary analysis region; at least one first working electrode including a first conductor and a reagent composition disposed in the reservoir; at least one first counter electrode including a second conductor and at least one first redox species disposed in a first secondary analysis region; and at least one second counterelectrode including a third conductor and at least one second redox species disposed in a second secondary analysis region, where the working electrode, the first counter electrode, and the second counter electrodes are independently addressable.

An analyte test sensor is disclosed that includes at least two substrates forming a reservoir, the reservoir including at least three independently addressable secondary analysis regions, were each of the secondary analysis regions are substantially chemically isolated.

In one aspect, a test sensor may be configured where a straight line passing from the working electrode through the first secondary analysis region and through the primary area cannot be drawn through the second secondary analysis region to the counter electrode. A test sensor also may be configured where a conductor is disposed between two substrates and at least one portion of a reservoir including a sample port is defined at least by the two substrates and an edge of the conductor. In this instance, the edge of the conductor defines at least a first electrode.

In another aspect, a test sensor may be configured where a fluid sample entering the at least one sample port does not flow across more than one of the first, the second, and the third electrodes to reach another electrode. A test sensor also may be configured where mixing of the first and the second redox species is not observed by an analysis technique selected from cyclic voltammetry and chemoamperometry within 12 minutes if the test sensor is not mechanically disturbed or within 1.4 minutes if the test sensor is mechanically disturbed.

A method of measuring at least one analyte in a sample is disclosed that includes chemically or biochemically oxidizing or reducing at least one analyte in a sample; applying a first input signal to the sample with at least a first working electrode and a first counter electrode; applying a second input signal at a different potential than the first input signal to the sample with at least the first working electrode and a second counter electrode; analyzing the output signals from the first and the second input signals to determine a concentration of a first measurable species in the sample at the potential of the first counter electrode, and a concentration of a second measurable species in the sample at the potential of the second counter electrode; and converting at least one of the first and the second measurable species concentrations into the concentration of the at least one analyte in the sample.

A method of measuring at least one analyte in a sample is disclosed that includes introducing the sample to a test sensor including at least two pairs of electrodes, the at least two pairs of electrodes including at least four independently addressable and substantially chemically isolated electrodes, where at least two of the electrodes are working electrodes and at least two of the electrodes are counter electrodes; chemically or biochemically oxidizing or reducing the analyte in the sample; applying a gated input signal to the sample across the at least two pairs of electrodes to generate at least two output signals; combining the at least two output signals; and measuring the concentration of the analyte in the sample from the combined output signals. Systems of using the disclosed test sensors with the disclosed methods also are disclosed.

Other devices, systems, methods, features and advantages of the invention will be, or will become, apparent to one with skill in the art upon examination of the following figures and detailed description. It is intended that all such additional systems, methods, features, and advantages be included within this description, be within the scope of the invention, and be protected by the claims that follow.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 3A represents a straight-channel test sensor design where the sample flows from a primary area across a first potential electrode location to reach a second potential electrode location.

FIG. 3B through FIG. 3G represent alternate designs for secondary analysis regions where the sample does not flow across more than one potential electrode location.

DETAILED DESCRIPTION

A biosensor system including test sensors having at least three independently addressable analysis regions is disclosed. Each analysis region includes a conductor or electrode and may be substantially chemically isolated. Thus, the working and counter electrodes of an electrode pair may reside in substantially chemically isolated environments. A working electrode may be combined with two or more counter electrodes, where each counter electrode resides in a substantially chemically isolated environment. Thus, the system may include at least two counter electrodes operating at different potentials. The independent addressability of the substantially chemically isolated analysis regions provides for multi-potential electrochemical analysis.

Operating at more than one potential, samples including multiple analytes may be analyzed. Multiple, independent analyses of the same analyte may be performed to increase the accuracy and/or precision of the analysis. In addition to multi-analyte and multi-analysis, the configurability of the system allows for increased accuracy and/or precision as the portion of the output signal attributable to sample interferents, hematocrit, mediator background, temperature, manufacturing variability, reagent deactivation, and the like may be determined. Analyte interferents are chemical, electrochemical, physiological, or biological species that result in a positive or negative bias in the determined analyte concentration. Once known, these effects may be used to alter or may be removed from the determined analyte concentration. Calibration information also may be provided by analysis regions that are not responsive to an analyte.

Figure 1A:
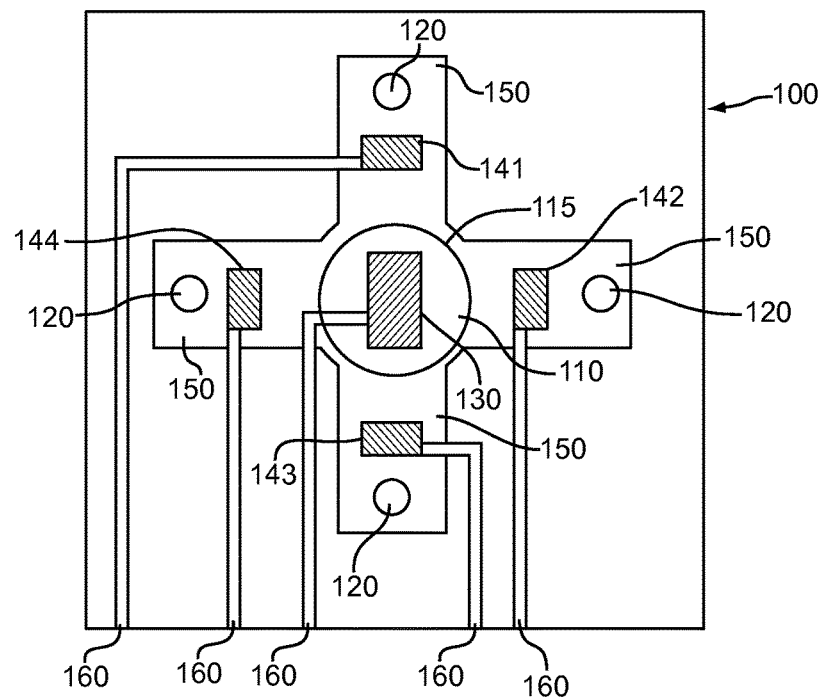
FIG. 1A represents a test sensor arrangement where the sample is introduced to the top of a primary area through a sample port and flows in a substantially symmetrical manner to fill four secondary analysis regions.

FIG. 1A represents a test sensor 100 arrangement where the sample is introduced to the top of a primary area 110 through a sample port 115 and flows in a substantially symmetrical manner to fill four secondary analysis regions 150. Each of the secondary analysis regions 150 includes a vent 120 to allow the sample to exhaust air from the secondary analysis regions 150 during filling. The vent 120 may be any shape that is compatible with the shape of the secondary analysis regions 150, such as circular or polygonal. The maximum diameter or width of the vent 120 may be any size that provides the desired sample flow into the secondary analysis regions 150, with values from about 0.02 mm to about 1.5 mm being preferred.

Figure 1B:
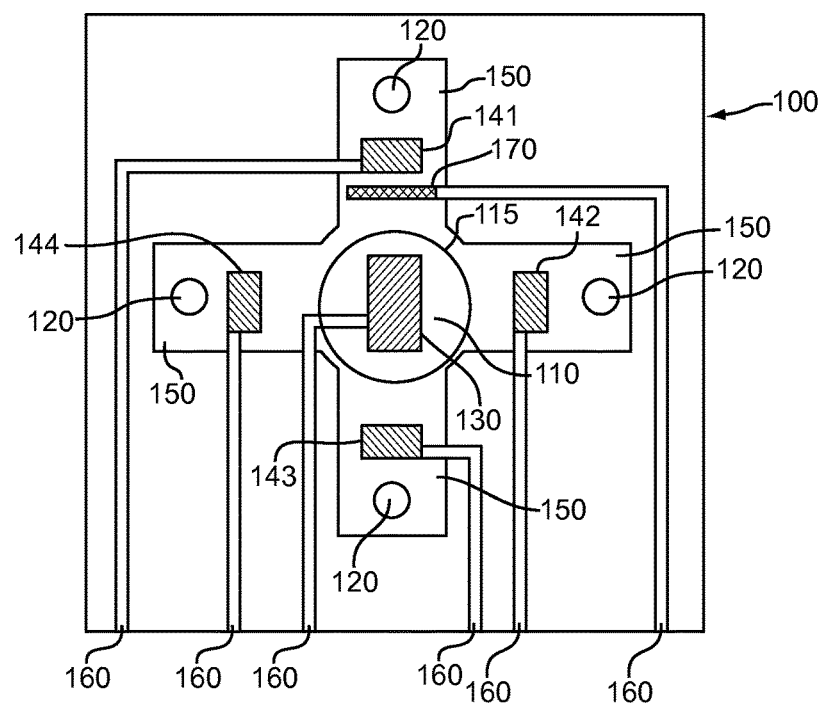
FIG. 1B represents the test sensor of FIG. 1A with the addition of a reference electrode.

A single counter electrode 130 occupies the primary area, while a working electrode 141-144 is present in each secondary analysis region 150. While depicted with the counter electrode 130 in the primary area 110 and the working electrodes 141-144 in the secondary analysis regions 150, the positioning of the working and counter electrodes could be reversed so multiple counter electrodes surround a single working electrode (not shown). In another aspect, the electrodes may not occupy the same plane. For example, some electrodes may be arranged horizontally while others are arranged vertically. In another example, some electrodes may be placed higher than others so the biological fluid reaches the lower electrodes first. Other electrode configurations may be used. For example, FIG. 1B represents the test sensor of FIG. 1A with the addition of a reference electrode 170 to provide a non-variant potential.

Figure 1C:
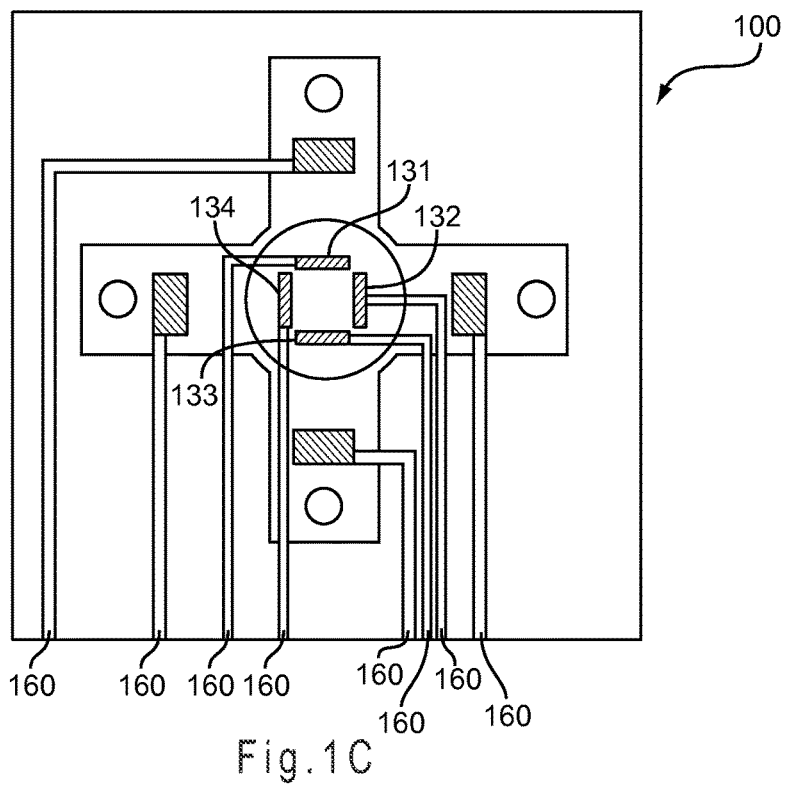
FIG. 1C represents the test sensor of FIG. 1A with separate counter electrodes.

FIG. 1C represents the test sensor 100 where instead of a single counter electrode 130, four independent counter electrodes 131-134 are provided in the central primary area 110. While depicted with the counter electrodes in the primary area and the working electrodes in the secondary analysis regions, the positioning of any working electrode and any counter electrode may be reversed (not shown). Other electrode configurations may be used.

Figure 1D:
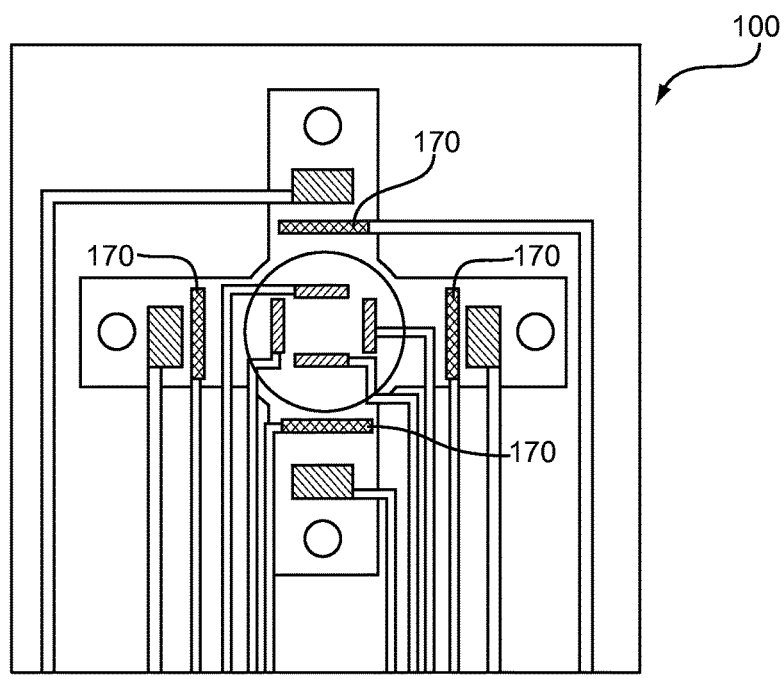
FIG. 1D represents the test sensor of FIG. 1C with the addition of a reference electrode.

FIG. 1D represents the test sensor of FIG. 1C with the addition of a reference electrode 170 to each secondary analysis region to provide a non-variant potential. One or more of the reference electrodes 170 may operate at one or more potentials to provide a non-variant potential to each analysis. As the operating potential of the counter electrodes may vary, one or more reference electrode may be used to reference the potential at the counter electrodes in addition to referencing the potential of the working electrodes as common in conventional systems.

Although not shown in the figure, for test sensors implemented in continuous monitoring applications, such as for electrodes implanted in a living organism or otherwise in continuous contact with a biological fluid, the use of multiple reference electrodes may provide for increased accuracy and/or precision of the determined analyte concentrations. The increase may arise from a reduction in the problems associated with the changing potential of working electrodes implanted in a living organism or otherwise in continuous contact with a biological fluid.

In FIG. 1A and FIG. 1B, conductors 160 lead from each electrode toward the rear of the test sensor 100 where each of the conductors 160 may be connected to a measurement device, allowing for each working electrode 141-144 to be independently addressed. Thus, when the conductor 160 is connected to a single electrode, the electrode is independently addressable. The conductors 160 may remain independently addressable or any two or more may be electrically connected (not shown). Thus, when more than one electrode is electrically connected to the same conductor, the electrodes are not independently addressable as they are electrically addressed together. For example, by electrically connecting two of the working electrodes 141-144, such as 141 and 144, the resulting test sensor 100 would have three independently addressable working electrodes and one counter electrode 130.

When configured with the single counter electrode 130 and four independently addressable working electrodes 141-144, the test sensor 100 of FIG. 1A and FIG. 1B may potentially perform a different analysis at each of the working electrodes 141-144. The single counter electrode 130 may provide a single potential to the system through the use of a charge transfer system that operates at a single potential. Depending on the measurement device, the single counter electrode 130 may provide more than one potential to the system.

If the electrode types were reversed for the test sensor 100 of FIG. 1A and FIG. 1B so there were four independently addressable counter electrodes and a single working electrode, the electrochemistry at the working electrode potentially could be measured at four different potentials. The independent addressability of the counter electrodes allows for each counter electrode to be formed with a different charge transfer system, thus altering the potential provided to the working electrode during analysis. If the working electrode includes reagents that interact with one or more analytes at four different potentials, each analyte interaction may be independently measured by electrically addressing the appropriate counter electrode. Preferably, each independently addressable counter electrode operates at a single potential or potential range.

In FIGS. 1C and 1D, the conductors 160 lead from each electrode toward the rear of the test sensor 100 where each of the conductors 160 may be connected to a measurement device. This arrangement allows for each working electrode 141-144 and each counter electrode 131-134 to be independently addressed. The conductors 160 may remain electrically isolated or any two or more may be electrically connected (not shown). For example, by electrically connecting two of the counter electrodes, such as 132 and 133, the resulting test sensor would have four independently addressable working electrodes and three independently addressable counter electrodes. Any combination of electrodes may be electrically connected.

Independently addressable working electrodes potentially allow for a different chemical reaction to be measured at each working electrode 141-144. Having independently addressable counter electrodes 131-134 of differing operating potentials allows for a working electrode to be operated against more than one counter electrode potential. Thus, two charge transfer chemistries present at the same working electrode may be measured independently by two independently addressable counter electrodes where the first counter electrode operates at the potential of the first charge transfer chemistry and the second counter electrode operates at the potential of the second charge transfer chemistry.

The test sensor 100 of FIG. 1C provides independent addressability to four working electrodes 141-144 and four counter electrodes 131-134. Because each of the counter electrodes 131-134 may provide a different potential, sixteen different analyses potentially may be performed. Thus, the electrochemistry of a single working electrode may be measured at four different potentials and the potential of a single counter electrode may be applied against four different working electrode chemistries. The test sensor of FIG. 1D, having four independently addressable reference electrodes 170, may provide up to four different non-variant potentials to the system. The measurement device may use one or more of the non-variant potentials to control or determine the operating potential at the working electrodes 141-144 and at the counter electrodes 131-134.

For the test sensor 100 of FIG. 1A through FIG. 1D, the secondary analysis regions 150 may have areas of about 0.5 mm² and heights of about 0.125 mm to provide interior volumes of about 62 nL each. Preferable secondary analysis regions have interior volumes of 100 nL and less, with interior volumes of 70 nL and less being more preferred. Larger and smaller secondary analysis regions may be used.

Figure 2A:
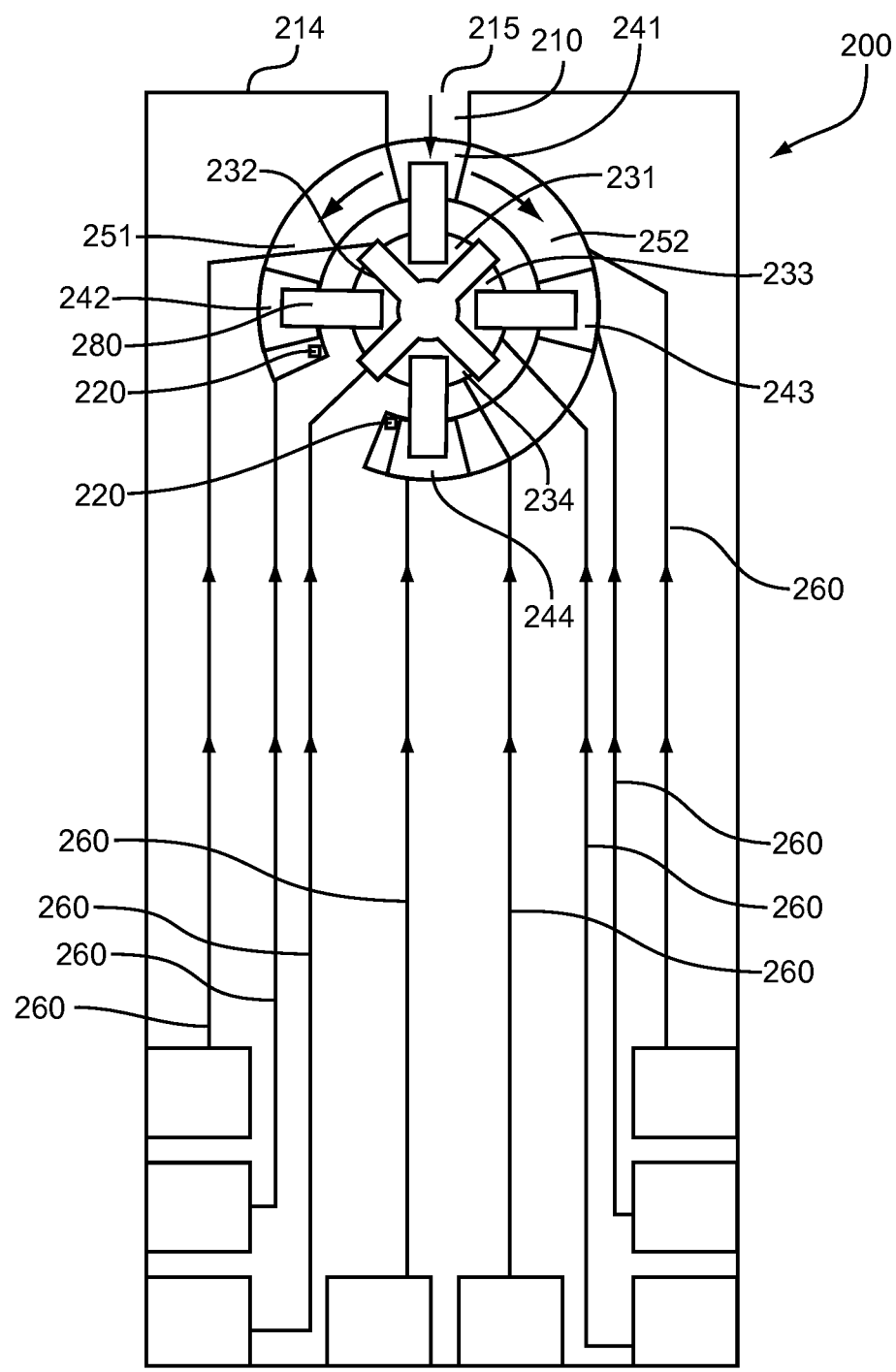
FIG. 2A represents a test sensor arrangement where sample introduction occurs from a sample port in a side of the test sensor into a primary area and then flows in an asymmetric manner to fill two secondary analysis region.

FIG. 2A represents a test sensor 200 arrangement where sample introduction occurs from a sample port 215 in a front edge 214 of the test sensor 200 into a primary area 210 and then flows in an asymmetric manner to fill a first secondary analysis region 251 and a second secondary analysis region 252. Sample flow is asymmetric because the second secondary analysis region 252 is longer than the first secondary analysis region 251. The secondary analysis regions 251, 252 may include a vent 220 to allow the sample to exhaust air from the region during filling.

On entry, the sample crosses a first electrode pair defined by working electrode 241 and counter electrode 231. While continuing to cross the first electrode pair, the sample flows toward the second and third electrode pairs, defined by working electrode 242 and counter electrode 232 (second pair) and by working electrode 243 and counter electrode 233 (third pair). The sample flowing across the first and third electrode pairs then continues to flow until crossing the fourth electrode pair, defined by working electrode 244 and counter electrode 234. Thus, the fourth electrode pair is crossed by the sample after the first and third electrode pairs. When crossed by the sample, a reagent composition 280 provides electrical conductivity between the pairs of the working and counter electrodes. Independent addressability of the electrode pairs allows for the filling of the secondary analysis regions 251, 252 to be monitored. Other electrode configurations may be used, for example the positioning of any working electrode and any counter electrode may be reversed (not shown).

By monitoring the filling of the secondary analysis regions 251, 252, the test sensor 200 provides an underfill detection system to prevent or screen out analyses associated with sample sizes that are of insufficient volume. Because concentration values obtained from an underfilled test sensor may be inaccurate, the ability to prevent or screen out these inaccurate analyses may increase the accuracy of the concentration values obtained. Conventional underfill detection systems have one or more indicator, such as an electrode or conductor, which detect the partial and/or complete filling of the sample reservoir within the test sensor. Having the ability to monitor filling between multiple secondary analysis regions, more accurate determinations of the fill state of the test sensor 200 are possible. The electrical signal may be used to indicate whether a sample is present and whether the sample partially or completely fills a specific analysis region.

Figure 2B:
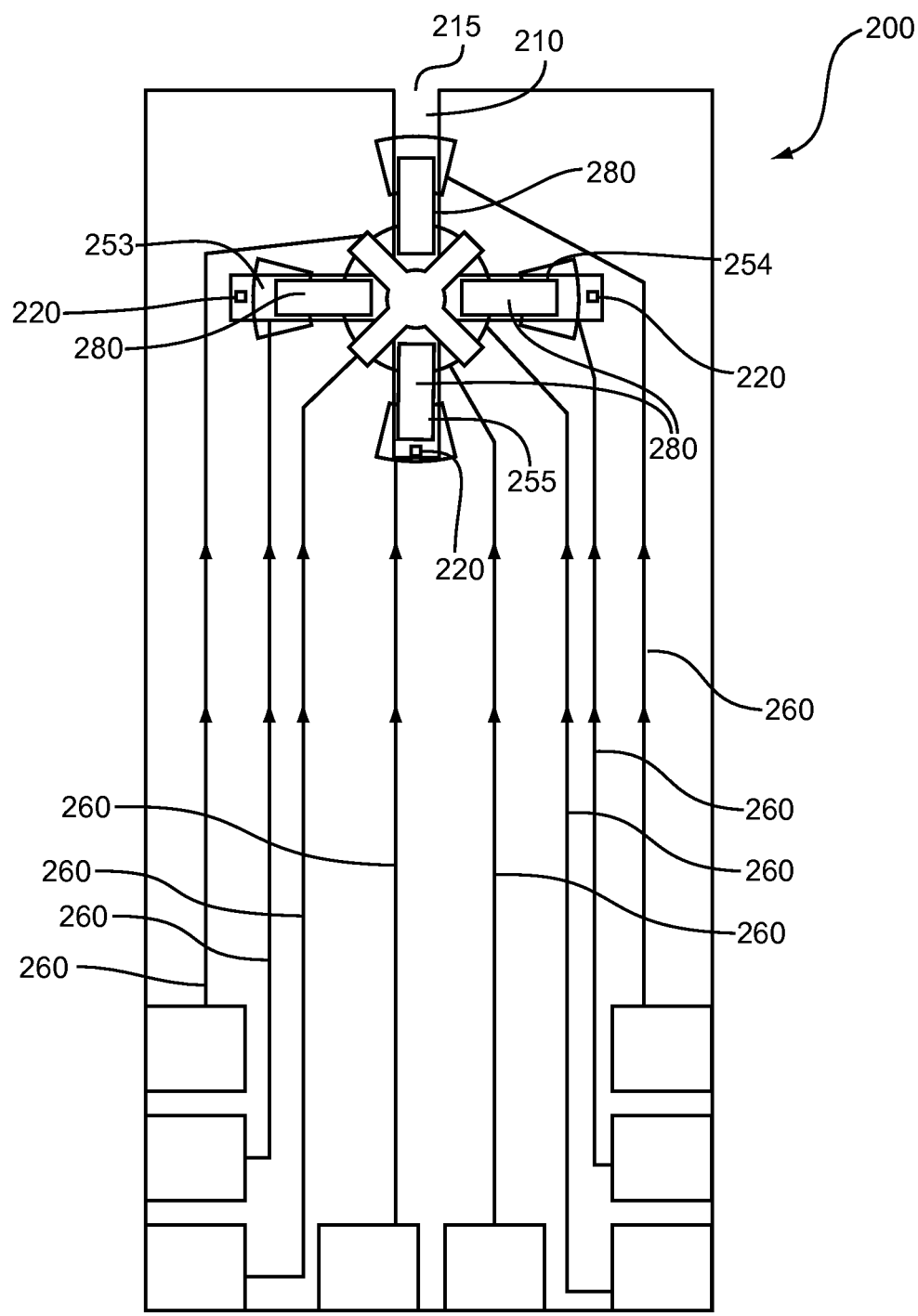
FIG. 2B represents a test sensor having the electrode arrangement of FIG. 2A, but with a different arrangement of the secondary analysis regions.

FIG. 2B represents the test sensor 200 having the electrode arrangement of FIG. 2A, but with a different arrangement of the secondary analysis regions. A primary area 210 including the first electrode pair is provided with the three symmetrically filled secondary analysis regions 253, 254, 255. On entry, the sample crosses the first electrode pair and then moves independently to cross the second, third, and fourth electrode pairs. Overall, fluid flow remains asymmetric due to the first electrode pair occupying the primary area, thus filling before the secondary analysis regions. Each of the secondary analysis regions 253, 254, 255 may include a vent 220 to allow the sample to exhaust air during filling of the test sensor 200.

A single reagent composition 280 may extend between each of the four working and counter electrode pairs as shown. A conductor 260 leading from each electrode toward the rear of the test sensor 200 where it may be connected to a measurement device, allowing for each electrode to be independently addressed. While each electrode is independently addressable, each electrode pair share the same chemical environment due to the same reagent layer contacting both the working and counter electrodes of each pair. The electrodes may remain electrically isolated or any two or more may be electrically connected (not shown). One or more reference electrodes may be added to provide a non-variant potential (not shown).

While depicted with the counter electrodes centrally grouped and the working electrodes around the perimeter, the positioning of any working and counter electrode may be reversed. The four independent working electrodes provide for four different reagent compositions to potentially perform four different analyses. While the four independent counter electrodes each may be operated at a different potential to provide 16 possible analyses, the 90° separation between each electrode pair may make this impractical.

FIG. 3A represents a straight-channel test sensor design where the sample flows from primary area 310 across a first potential electrode location 320 to reach a second potential electrode location 330. FIG. 3B through FIG. 3G represent alternate test sensor designs for secondary analysis regions where the sample does not flow across more than one potential electrode location. FIG. 3B represents a T-channel design used in some conventional sensors. FIG. 3C represents a multi-T-channel design where additional potential electrode locations 340 and 350 are present. Additional "T" portions may be added if additional potential electrode locations are desired.

Figure 3H:
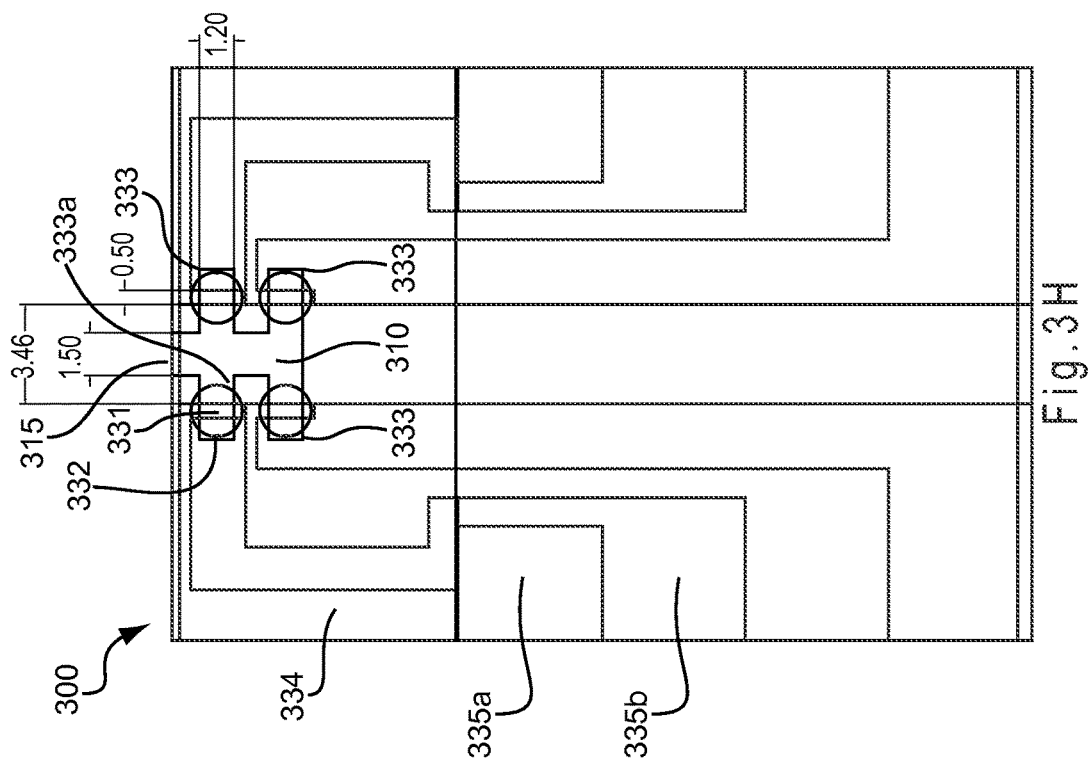
FIG. 3H depicts a multi-T-channel test sensor having both an independently addressable working electrode and an independently addressable counter electrode in each of four secondary analysis regions.

FIG. 3H depicts a multi-T-channel test sensor 300 having both an independently addressable working electrode 331 and an independently addressable counter electrode 332 in each of four secondary analysis regions 333. Thus, each working and counter electrode pair shares the same chemical environment, but each pair of electrodes is substantially chemically isolated from every other pair. A combined reagent composition charge transfer system 336 is deposited on each electrode pair. Each of the working electrodes 331 and each of the counter electrodes 332 is formed from a conductor 334 that terminates in a contact 335. Contact 335a and contact 335b correspond to the working and counter electrodes, respectively, of the secondary analysis region 333a. The width of each of the secondary analysis regions 333 is 1.2 mm, while the width of primary area 310 is 1.5 mm. The straight-line distance between the electrode pairs in opposing secondary analysis regions is 3.46 mm. The width of the working electrode of each pair is specified to be 0.50 mm separated from the counter electrode by from about 0.05 mm to about 0.25 mm. The circles drawn on each of the working electrodes 331 is the projected coverage area of the reagent composition. Other secondary analysis region widths, electrode widths and separations, and reagent composition coverage areas may be used.

Figure 3I:
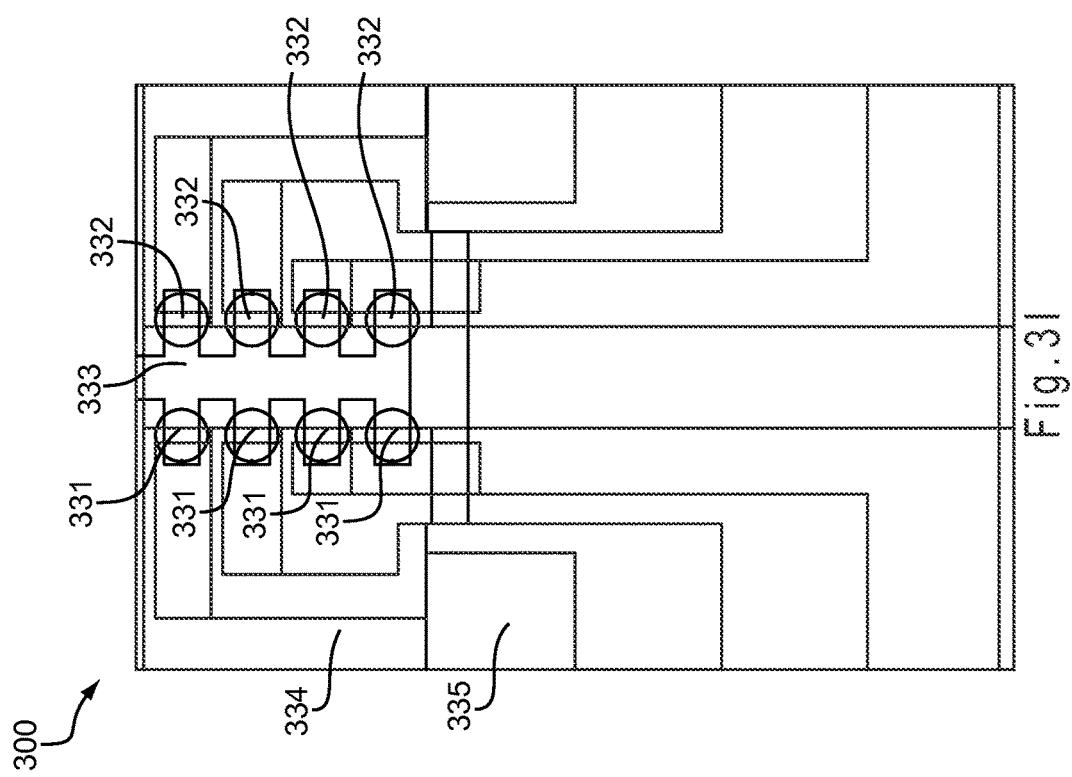
FIG. 3I depicts a multi-T-channel test sensor having an independently addressable working electrode in each of four substantially chemically isolated secondary analysis regions and an independently addressable counter electrode in each of four opposing secondary analysis regions.

FIG. 3I depicts a multi-T-channel test sensor 300 having an independently addressable working electrode 331 in each of four substantially chemically isolated secondary analysis regions and an independently addressable counter electrode 332 in each of four opposing secondary analysis regions 333. Thus, each electrode is substantially chemically isolated from every other electrode. Each electrode is formed from a conductor 334 that terminates in a contact 335.

FIG. 3D represents a departure from T-channel designs because the secondary analysis regions are staggered so a straight line 370 passing through the secondary analysis regions and a primary area cannot be drawn between any two potential electrode locations. The potential advantage of such a staggered design is the resistance to mixing between the opposing secondary analysis regions if the test sensor is mechanically disturbed while filled with the sample. Mechanically disturbed means applying a sufficient force to the test sensor to cause the fluid sample to move In addition to failing the straight line test, the Y-channel designs of FIG. 3E through FIG. 3G resist mixing between potential electrode locations that are closer together than for the designs of FIGS. 3B and 3C because the separation of the secondary analysis regions does not solely rely on the distance between potential electrode locations for substantial chemical isolation. Chemical separation in a Y-channel also may benefit from the sample having to flow around the "v" portion of the "Y" to mix. As the electrodes may be spaced closer together, but still resist sample mixing, the total volume of the sample reservoir of a Y-channel design may be less in relation to a T-channel design having a similar chemical separation.

Preferable sample reservoir designs have secondary analysis regions branching from the primary area 310 at an angle 390 of less than 90°, as represented in FIG. 3F. In this manner, fluid may enter the test sensor and reach the potential electrode locations without making a 90° turn. This may allow for the sample to rapidly enter the test sensor while reducing the potential for reagent mixing from sample convection due to vibration. More preferable designs lack the straight line 370 as depicted in FIG. 3B and FIG. 3C between electrodes passing through the secondary analysis regions and a primary area and have secondary analysis regions branching from the primary area at an angle of less than 90°. Other designs, such as those having one or more bends in the primary area and/or secondary analysis regions and those where the secondary analysis regions branch from the primary area at an angle of greater than 90° also may be used; however, increasing sample size requirements and slower sample filling speeds may be limiting factors.

Figure 3J:
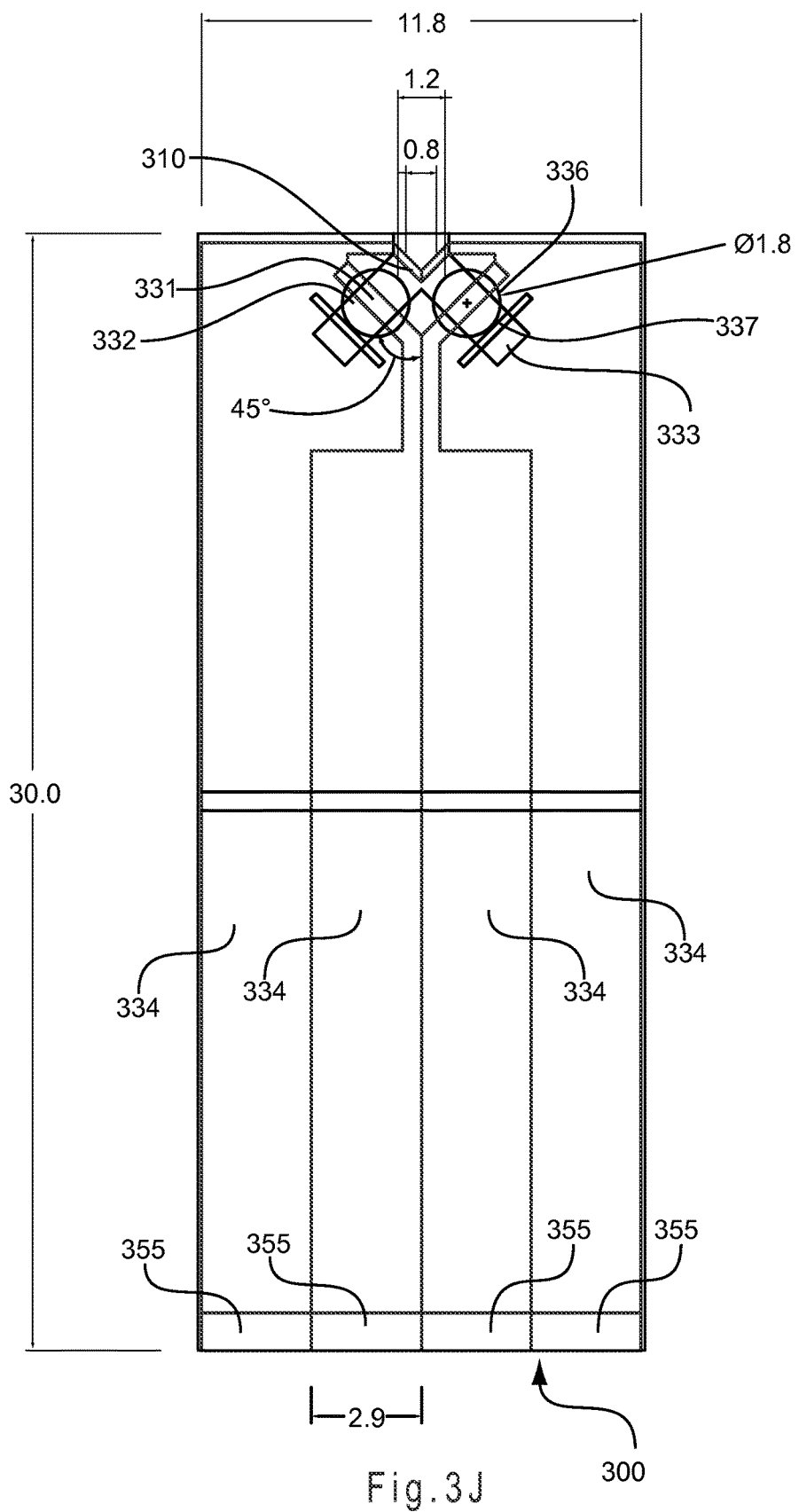
FIG. 3J depicts a Y-channel test sensor having both an independently addressable working electrode and an independently addressable counter electrode in each of two secondary analysis regions.

FIG. 3J depicts a Y-channel test sensor 300 having both an independently addressable working electrode 331 and an independently addressable counter electrode 332 in each of two secondary analysis regions 333. Thus, each working and counter electrode pair of electrodes share the same chemical environment, but each pair is substantially chemically isolated from the opposing pair. While the working electrode 331 crosses the secondary analysis region 333, the counter electrode 332 is defined by the perimeter edge of the secondary analysis region 333, which is in turn formed from the conductor 334. The secondary analysis regions 333 branch from the primary area 310 at an angle of about 45°. Each of the conductors 334 terminate in a contact area 335. Other electrode designs could be used, such as those in which a single electrode is formed in one or more secondary analysis regions. Other branching angles for the secondary analysis regions also may be used.

The substrate of the test sensor 300 has a width of 11.8 mm and a length of 30 mm. The width of the primary area 310 is 1.2 mm. The distance between the projected outer edges of the two reagent composition depositions is 0.8 mm. The contact areas 335 each have a width of 2.9 mm and the diameter of the reagent composition deposition in each of the two secondary analysis regions 333 is 1.8 mm. Other substrate dimensions, primary area and contact area widths, and reagent composition deposition diameters may be used.

In addition to the number and type of electrodes and the degree of independent electric addressability of the electrodes, the degree of chemical isolation provided by the secondary analysis regions of the sample reservoir affects the number of analyses that may be performed with a test sensor. Substantially chemically isolated means that diffusive or convective mixing of the reagents does not substantially occur between the secondary analysis regions during the time of the one or more analyses.

If a working and counter electrode pair is substantially chemically isolated from other working and counter electrode pairs, but not from each other, the pair may perform analyses compatible with the chemistry present at the pair. Such a configuration may allow for rapid diffusive mixing of the reagents present at the working and counter electrodes of the pair. Conversely, if working and counter electrodes are substantially chemically isolated from other working and counter electrodes and from each other, each electrode potentially may participate in an analysis with any other electrode, if independently addressable. Thus, if substantially chemically isolated, different reagent compositions may be used to provide an electrode with a chemical analysis environment that is different from other electrodes. In combination, substantial chemical isolation between analysis regions allows different reagents to be used at each working and/or counter electrode, while the independent electrical addressability allows each working electrode to be independently measured.

The secondary analysis regions may be substantially chemically isolated depending on the cross-sectional area of the entrances to the secondary regions, the distances between any two electrodes within the secondary analysis regions, the physical arrangement of the secondary analysis regions in relation to each other and in relation to the primary area, and the like. In addition to these concerns, substantial chemical isolation initially may be lost due to reagent mixing as the sample flows across the counter electrode/s (FIG. 1A through FIG. 1D) or the electrode pairs at the entrance and at the sides of the test sensor (FIG. 2A and FIG. 2B). In this manner, reagent composition may be transported by the sample to multiple electrode pairs. Conversely, such flow mixing may be substantially eliminated when the sample does not flow across more than one electrode (FIG. 3B-FIG. 3J).

Figure 4A:
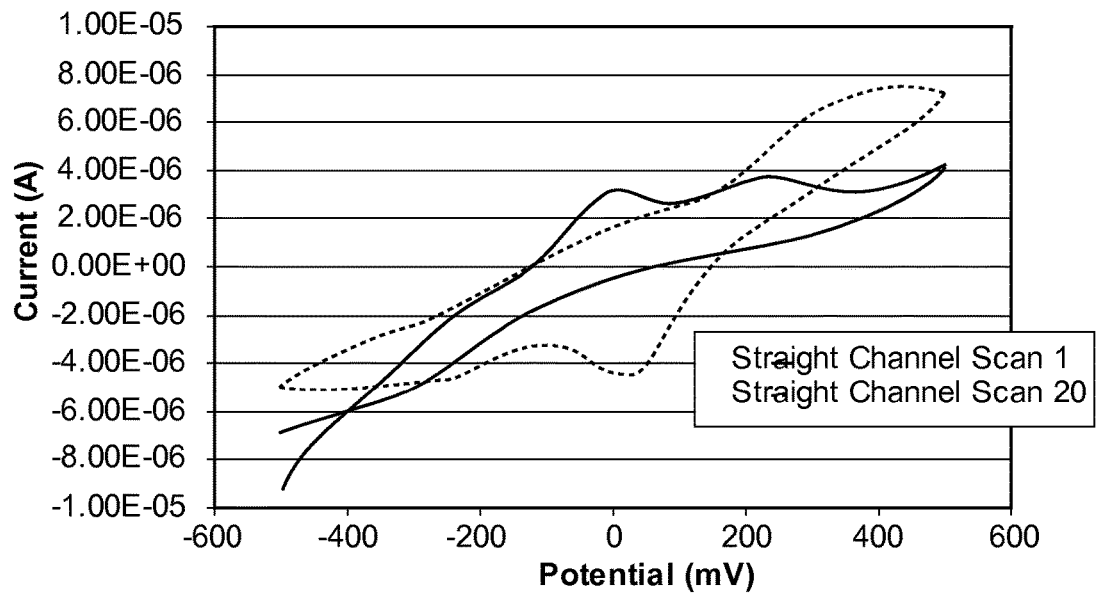
FIG. 4A shows the cyclic voltammogram of a straight-channel test sensor design, such as represented in FIG. 3A.

FIG. 4A shows the cyclic voltammetry plot of a straight-channel design as represented in FIG. 3A. The first electrode pair nearest the sample port used a reagent composition including 0.5 M potassium ferrocyanide, while the second electrode pair nearest the terminus of the channel used a reagent composition including the electro-active organic molecule represented by Structure I, below. Within about seven seconds or less, two peaks were observed, with the left peak representing oxidation of the reduced state of the Structure I molecule and the right peak representing oxidation of ferrocyanide, which was initially disposed at the first electrode pair. Within about 20 complete cycles, the Structure I molecule peak disappeared, suggesting that ferricyanide was oxidizing the Structure I molecule.

During the analysis, it is believed that ferrocyanide from the first electrode pair was oxidized at the second electrode to form ferricyanide at the second electrode pair. The formed ferricyanide then chemically oxidized the reduced species of the Structure I molecule at the second electrode pair. These results established that chemical contamination between the electrode pairs rapidly occurs in a straight-channel design. The experiment demonstrates that the stronger oxidizing agent, such as ferricyanide in this instance, will take over mediation from other mediators, such as the Structure I molecule, if the electrodes are not substantially chemically isolated. This contamination is believed attributable to a combination of the sample crossing the counter electrode before reaching the working electrode, diffusion, and convection within the straight-channel reservoir.

Figure 4B:
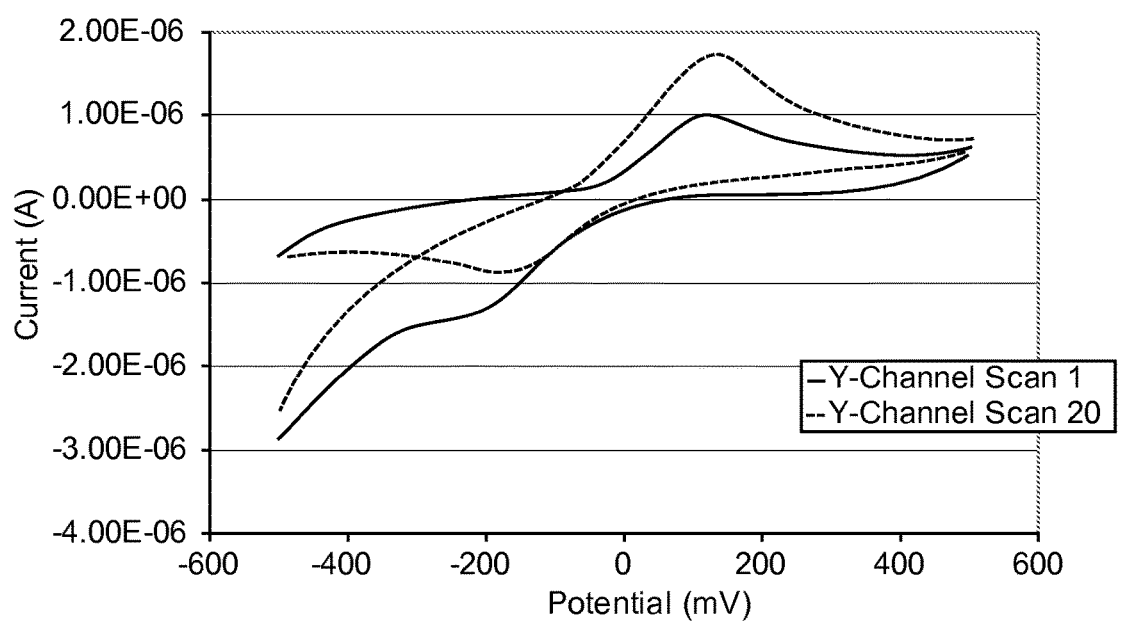
FIG. 4B shows the cyclic voltammogram of a Y-channel design, such as represented in FIG. 3E.

In contrast, FIG. 4B shows the cyclic voltammograms of a Y-channel design as represented in FIG. 3E. An electrode was placed near the terminus of each secondary analysis region. Only oxidation of the Structure I molecule is observed after 20 complete cycles (more than 20 minutes), establishing that substantial chemical isolation was achieved for at least 10 minutes with the Y-channel secondary analysis region design. These experiments were performed using a CH Instruments Electrochemical Workstation, model CHI 660A running version 2.05 software, at about 22° C. and a relative humidity of about 45%. The sample was pH 7.0 phosphate buffer containing 0.1 M sodium phosphate and about 16% (w/w) PVP polymer having a weight average molecular weight of about 2000.

Figure 5A:
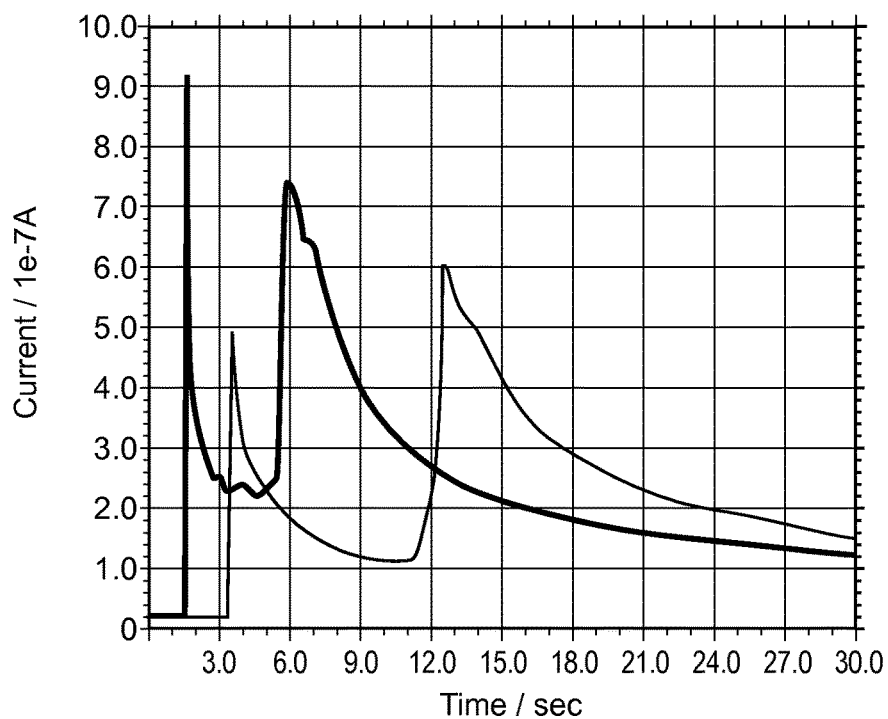
FIG. 5A shows a chemoamperometry current verses time plot establishing that for a straight-channel test sensor of the type used in FIG. 4A, a ferrocyanide peak was observed at the working electrode within about 5 seconds of introducing the sample.
Figure 5B:
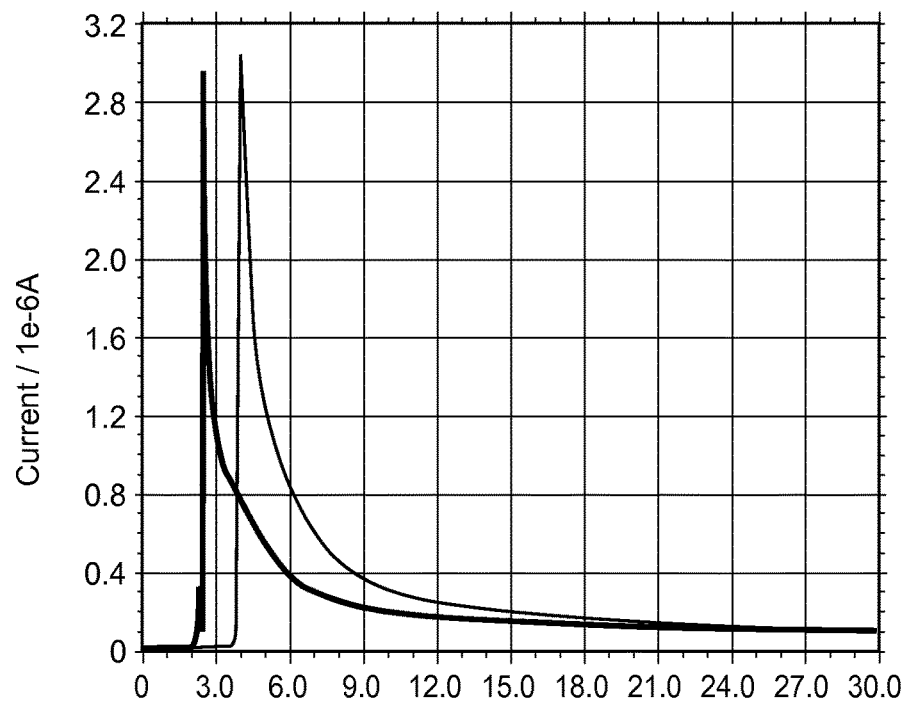
FIG. 5B shows a chemoamperometry current verses time plot establishing that for a Y-channel test sensor of the type used in FIG. 4B, substantially no ferrocyanide reached the working electrode after 30 seconds of introducing the sample.

A similar effect was observed for chemoamperometry testing, where current is measured as a function of time. In FIG. 5A a current verses time plot established that for a straight-channel sensor of the type used in FIG. 4A, a second peak was observed with a 400 mV operating potential at the working electrode within about 5 seconds of introducing the sample. Sample introduction generated the first peak in the plot. The second peak correlates with the second voltammetric wave of ferrocyanide in FIG. 4A. In FIG. 5B, it was shown that substantially no ferrocyanide reached the working electrode after 30 seconds, establishing that substantial chemical isolation was achieved with the Y-channel secondary analysis region test sensor. In these experiments, the initial sharp peak represented the sample first establishing electrical communication between the electrodes. The amperometry testing was performed using the CH Instruments Electrochemical Workstation at about 22° C. and a relative humidity of about 45%. The sample was pH 7.0 phosphate buffer containing 0.1 M sodium phosphate and about 16% (w/w) PVP polymer having a weight average molecular weight of about 2000.

Figure 5C:
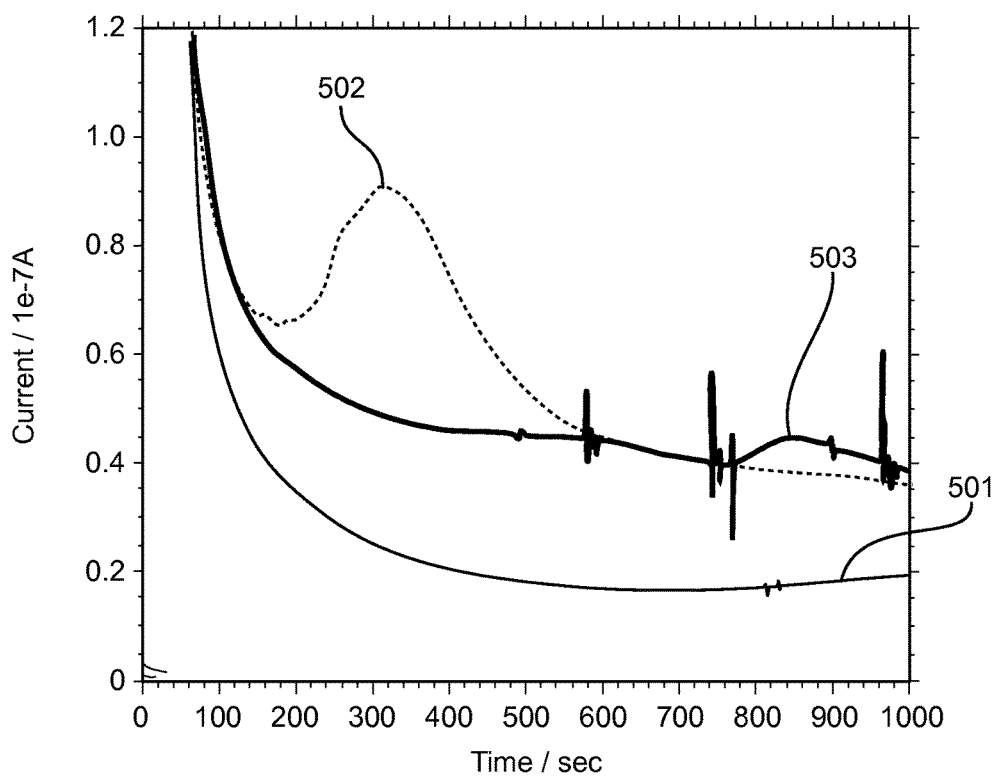
FIG. 5C is a chemoamperometry current verses time plot establishing that the Y-channel design provides superior chemical isolation between potential electrode locations than a T-channel design.
Figure 5D:
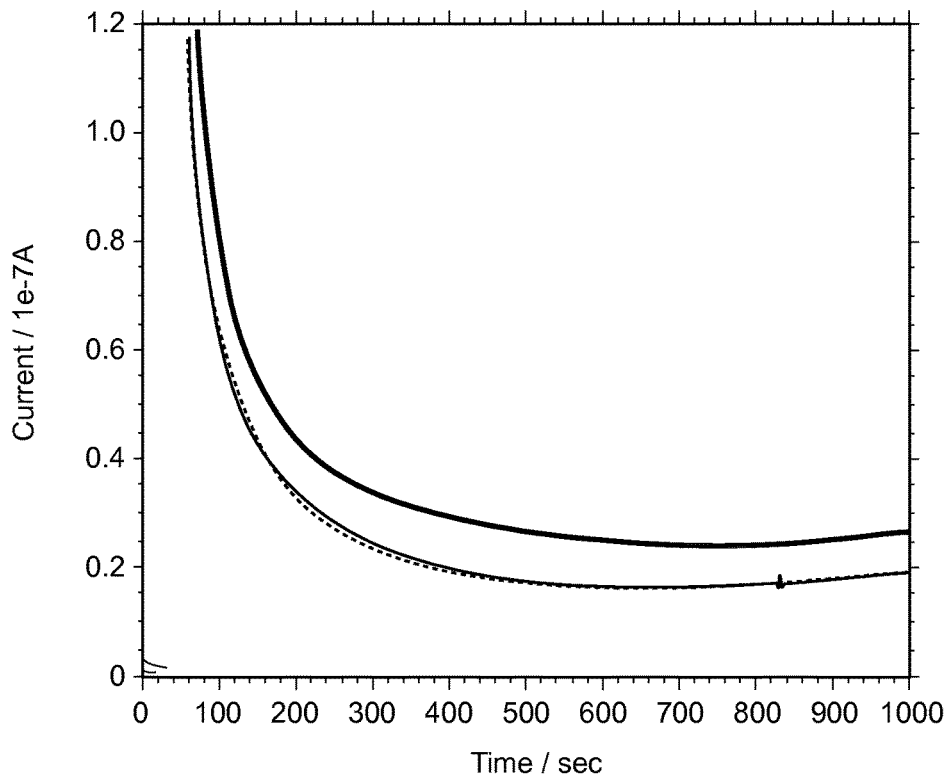
FIG. 5D establishes that three Y-channel designs were resistant to such mixing from mechanical disturbance.

FIG. 5C is an amperometric current plot establishing that the Y-channel design provides superior chemical isolation between potential electrode locations than a T-channel design. As shown by Y-channel line 501, substantial chemical isolation was observed out to 1000 seconds between the potential electrode locations, as represented by positions 320 and 330 of FIG. 3E. In contrast, as shown by T-channel peaks 502, 503 chemical isolation failure and oxidation of the Structure I molecule was observed after about 84 or after about 650 seconds for two T-channel test sensors, such as represented in FIG. 3B. The large variability between the 84 and 650 second time variables may be attributed to the susceptibility of the T-channel design to mixing by convection from mechanical disturbance during the analysis. FIG. 5D establishes that three Y-channel designs were resistant to such mixing from mechanical disturbance. The slow current rise observed after about 800 seconds may indicate slow mixing by diffusion.

Figure 6A:
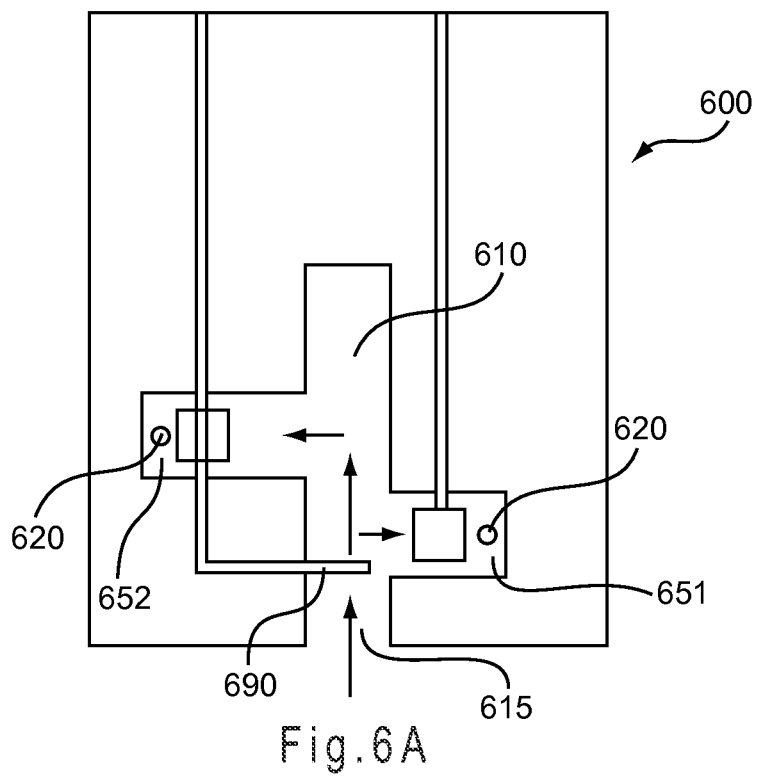
FIG. 6A represents a test sensor having a staggered arrangement of the secondary analysis regions where the sample enters a sample port into a primary area in the form of a channel from which two secondary analysis regions branch.
Figure 6B:
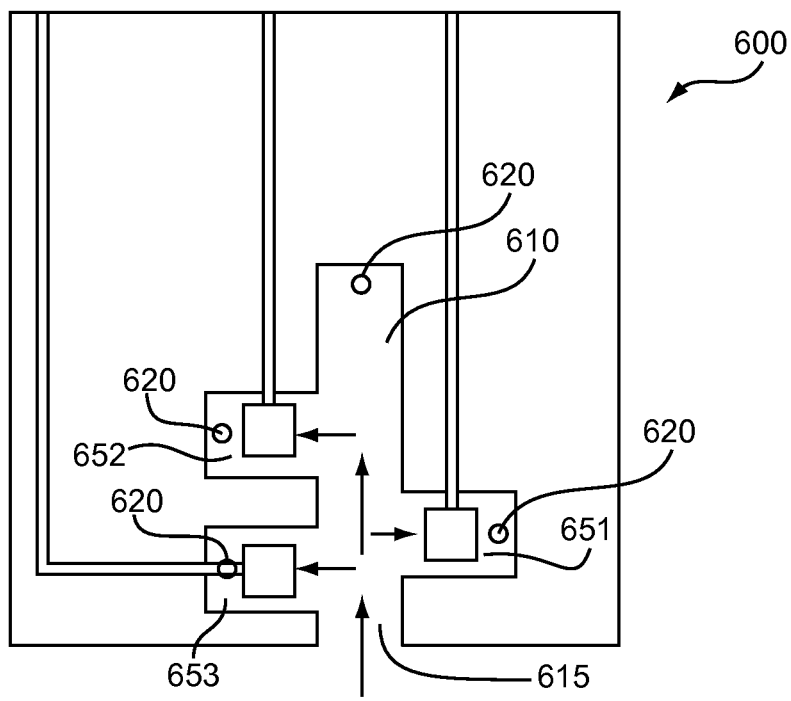
FIG. 6B represents a test sensor arrangement where the sample enters the sample port into a primary area in the form of a channel from which three secondary regions branch.

FIG. 6A represents a test sensor 600 having a staggered arrangement of the secondary analysis regions 651, 652 where the sample enters a sample port 615 into a primary area 610 in the form of a channel from which the two secondary analysis regions 651, 652 branch. A conductor 690 may extend into the primary area 610 to provide underfill detection capability to the test sensor 600. Similarly, FIG. 6B represents a test sensor arrangement where the sample enters the sample port 615 into a primary area 610 in the form of a channel from which three secondary regions 651-653 branch. Each of the secondary regions 651-653 includes an independently addressable electrode or conductor.

In FIG. 6A, the sample fills the first secondary region 651 on the right, then the second secondary region 652 on the left. In FIG. 6B, the sample fills the third secondary region 653 on the left, then the first secondary region 651 on the right, and then the second secondary region 652 on the left.

The total sample volume held by the test sensor 600 having at least two or three secondary analysis regions may be 210 nL or less. Each of the secondary analysis regions and the end of the primary area 610 opposite the sample port 615 may include a vent 620 to allow the sample to exhaust air during filling. By dividing the sample reservoir defined by the primary area 610 and the secondary analysis regions 651-653 into one or more primary areas that fill multiple secondary regions, the test sensor 600 may fill faster than a substantially undivided sample reservoir, such as the straight-channel design represented in FIG. 3A, of the same or similar volume due to the effect of capillary action driven by surface tension. Thus, subdividing the sample reservoir into smaller secondary analysis regions, where each may contain an electrode, an electrode pair, one or more conductors, or a combination thereof, may increase the fill rate for the test sensor 600. Substantial chemical isolation between the secondary regions during filling and during the analysis may be provided by filling the secondary regions from the primary area in this manner.

As the sample primarily flows to the nearest vent 620, the secondary regions 651-653 are filled in a substantially sequential manner from the primary area 610. Due to the sequential filling of the secondary regions 651-653, the measurement device can monitor the rate and flow of the sample as the secondary analysis regions 651-653 are filled. The flow of the sample also may be monitored by equipping the test sensor 600 with an electrode or conductor near the sample port 615 and/or near the vent 620 of the primary area 610. Thus, one or more conductor and/or electrode may be monitored by the measurement device to determine the fill condition of the test sensor 600. The filling of non-sequential filling designs may also be monitored in this manner; however, the system may or may not be able to independently monitor the filling of each secondary analysis region.

While not shown in the figure, the primary area 610 may be provided with multiple sample ports 615 to allow the sample to be introduced from more than one location, such as at a perimeter and a top location. Similarly, the test sensor 600 may be provided with two or more separate sample reservoirs, each having a primary area and two or more secondary regions, to allow for multiple samples to be analyzed. By altering the vent structure of the reservoir, different samples may be introduced through multiple sample ports into the same reservoir, but remain substantially chemically isolated during the analysis. Other relationships between the primary area or areas and secondary regions may be used.

The primary area 610 and/or one or more secondary regions 651-653 may include flow-altering materials that modify the flow of the sample as it distributes through the sample reservoir. For example, hydrophilic and/or hydrophobic treatments, coatings, or materials may be used to preferably direct the flow path and/or fill rate of aqueous samples. In another aspect, the primary area 610 and/or the secondary regions 651-653 may include structural features, such as walls, grooves, or channels, which preferably direct the flow path and/or fill rate of the sample. In another aspect, materials that chemically or physically alter the composition of the sample may be placed in the primary area 610 and/or the secondary regions 651-653. For example, a material that filters red blood cells from the sample may be placed in a portion of the primary area to remove the cells before the sample reaches a secondary region.

Figure 7A:
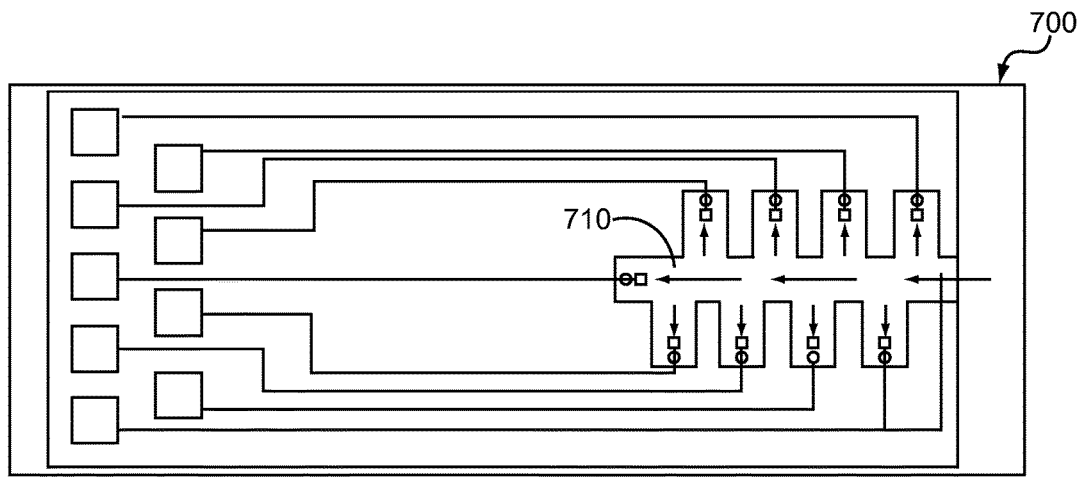
FIG. 7A and FIG. 7B represent test sensors having staggered secondary analysis region designs.
Figure 7B:
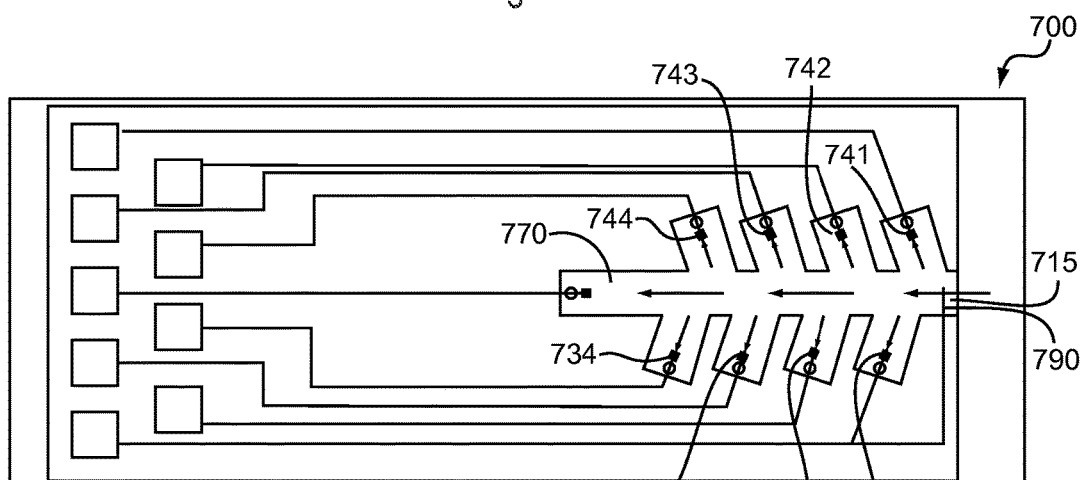

FIG. 7A and FIG. 7B represent test sensors 700 having staggered secondary analysis region designs as previously discussed. The design of FIG. 7A includes eight secondary analysis regions with approximately 90° angles to the primary area 710, while FIG. 7B is a similar Y-channel design. The test sensor 700 includes a total of nine secondary analysis regions, including the region at the end of primary area 710, each occupied by an electrode or conductor. The figure depicts four independently addressable counter electrodes 731-734 and four working electrodes 741-744, each present in one of the eight secondary regions. While the counter electrodes 731-734 reside on one side of the primary area 710 and the working electrodes 741-744 reside on the other side, the arrangement may be mixed. For example, the first two secondary analysis regions filled by the sample may be working electrodes while the second two secondary analysis regions filled by the sample may be counter electrodes.

An optional electrode, such as a reference electrode 770, is present at the end of the primary area 710 opposite sample port 715. The reference electrode 770 also could be placed in the rearmost secondary region in relation to where the sample is introduced or near the sample port 715, for example. Thus, one or more reference electrodes may be positioned in the primary area 710 and/or secondary regions to provide a non-variant potential to the system. Residing in a substantially chemically isolated environment from the secondary regions, optional electrodes may provide fill information or information about the sample.

A conductor 790 electrically connected to the counter electrode 731 is extended into the primary area 710 near the sample port 715. Although not independently addressable, the conductor 790 may provide fill information to the measurement device. Other configurations of electrodes and/or conductors are possible. Each secondary region and the end of the primary area 710 may include a vent (not shown).

The eight electrodes 731-734 and 741-744 may be addressed independently by the measurement device. As the secondary regions are substantially chemically isolated, each may include a reagent composition providing a different chemistry to interact with the constituents of the sample. Because the reagent composition may be different for each of the working electrodes 741-744, the charge transfer system may be different for each of the counter electrodes 731-734, and each electrode may be independently addressed, four different analyses may be possible when a single reagent composition is present at each of the working electrodes 741-744. In this manner, each working electrode reagent composition may be used with a dedicated counter electrode. Similarly, if each of the working electrodes 741-744 were provided with two reagent compositions having different redox potentials, a total of eight different analyses may be possible. Finally, providing each working electrode with four reagent compositions having different redox potentials may provide up to sixteen different analyses, as each working electrode may be independently addressed with each of the four counter electrodes. Practical considerations, such as unwanted interaction between more than one reagent composition at a working electrode, may limit the actual number of analysis that may be performed by the system. Other sample reservoir constructions and electrode configurations may be used.

Figure 8A:
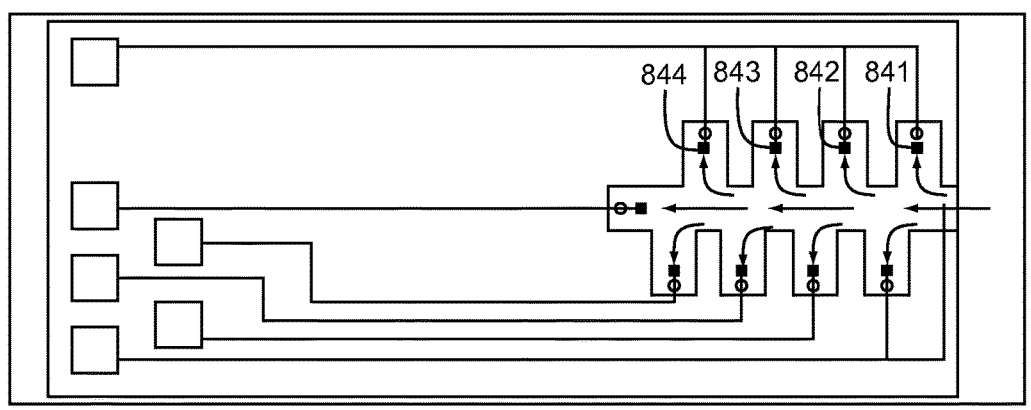
FIG. 8A represents a variation of the FIG. 7A test sensor where multiple working electrodes are electrically connected.

FIG. 8A represents a variation of the FIG. 7A test sensor where multiple working electrodes 841-844 are electrically connected. The counter electrodes remain independently addressable. In this manner, each counter electrode may provide a different potential to the electrically connected working electrodes. By electrically connecting one or more of the working electrodes, the working electrode having a redox potential closest to that of the potential of the selected counter electrode may operate. In this mode of operation, each working electrode may have a different mediator system, each mediator system having a different redox potential. By stepping the operating potential of the system from low to high using the different potentials of the counter electrodes, the different mediator systems of the working electrodes may be progressively addressed. Other sample reservoir constructions and electrode configurations may be used.

Figure 8B:
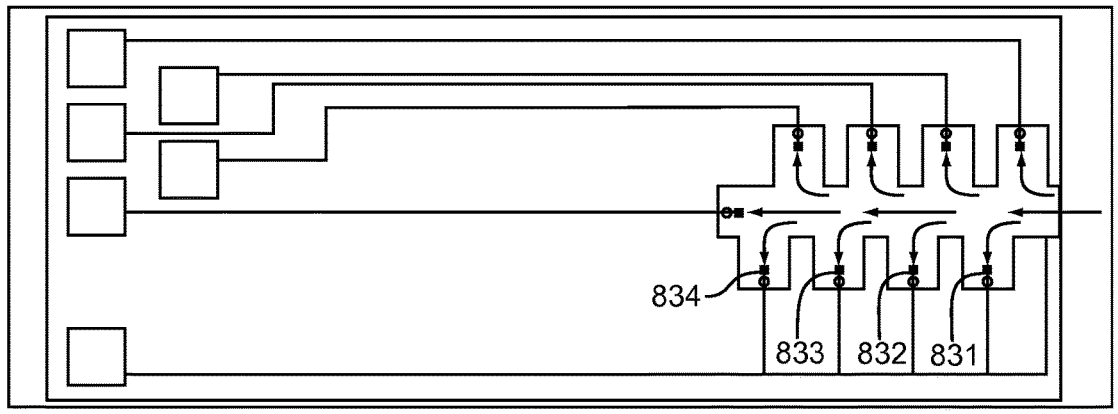
FIG. 8B represents a variation of the FIG. 7A test sensor where multiple counter electrodes are electrically connected.

FIG. 8B depicts a variation of FIG. 7A where multiple counter electrodes 831-834 are electrically connected. The working electrodes remain independently addressable. By electrically connecting one or more of the counter electrodes, the counter electrode having a charge transfer system with the highest potential may provide the potential to the system. In this manner, the electrochemistry responsive to the analyte at each working electrode may be measured. Other sample reservoir constructions and electrode configurations may be used.

With regard to the previously described test sensors, the working and counter electrodes present in the secondary analysis regions may be separated by 1,000 micrometers or more. Electrode separation distances less than 1,000 micrometers also may be used. The pattern of the electrodes is not limited to those shown in the figures, instead being any pattern compatible with the primary area and secondary analysis regions of the test sensor. Preferably, the electrodes are formed by a rectangular deposition of the reagent composition and/or a charge transfer system. The deposition may be made by screen printing, ink-jetting, micro-pipetting, pin-deposition, or other methods.

Reagent layers are formed when the reagent composition is applied to the conductor. For example, the reagent layer forming a working electrode may include an enzyme, a mediator, and a binder, while the reagent layer forming the counter electrode may include a mediator and a binder. Analytes undergo electrochemical reaction at the working electrode while the opposite electrochemical reaction occurs at the counter electrode to allow current flow between the electrodes. For example, if an analyte undergoes oxidation at the working electrode, reduction occurs at the counter electrode.

In addition to working and counter electrodes, test sensors may include reference electrodes that provide a non-variant reference potential to the system. While multiple reference electrode materials are known, a mixture of silver (Ag) and silver chloride (AgCl) is typical due to the insolubility of the metal and its corresponding salt in the aqueous environment of the sample. Since the ratio of Ag metal to Cl⁻ does not significantly change in the sample, the potential of the electrode does not significantly change. If increased in size and/or modified with a conductive metal, a reference electrode also may be used as a counter electrode because it will pass current. However, a counter electrode may not serve as a reference electrode because it lacks the ability to isolate the half cell that provides the reference potential from the sample solution.

The conductors that form the electrodes may reside on one or more substrates, depending on the arrangement of the electrodes. The substrate may be made from any material that is compatible with the formation and operation of the biosensor. Preferable materials for the substrate include polyethylene terephthalate (PET), polycarbonate (PC), polyimide (PI), polyethylene (PE), polypropylene (PP), polystyrene (PS), polyvinyl chloride (PVC), polyoxymethylene (POM), monomer-cast nylon (MC), polybutylene terephthalate (PBT), a polymethacrylic resin (PMMA), an ABS resin (ABS), and glass. More preferable materials from which to form one or more substrate include polyethylene terephthalate (PET), polycarbonate (PC), and polyimide (PI), with polyethylene terephthalate (PET) being preferred at present. To form a test sensor, two substrates in the form of a base and a lid may be combined to form a sample reservoir having at least one sample port and at least one vent. Conductors, spacers, and other components may reside between the substrates.

The material or materials used to form the conductors on the one or more substrates may include any electrical conductor. Preferable electrical conductors are non-ionizing, such that the material does not undergo a net oxidation or a net reduction during analysis of the sample. The conductors may be made from materials such as solid metals, metal pastes, conductive carbon, conductive carbon pastes, conductive polymers, and the like. The conductors preferably include a thin layer of a metal paste or metal, such as gold, silver, platinum, palladium, copper, or tungsten. A surface conductor may be deposited on all or a portion of the conductor. The surface conductor material preferably includes carbon, gold, platinum, palladium, or combinations thereof. If a surface conductor is not present on a conductor, the conductor is preferably made from a non-ionizing material.

The conductor and optional surface conductor material may be deposited on the substrate by any means compatible with the operation of the test sensor, including foil deposition, chemical vapor deposition, slurry deposition, metallization, and the like. In another aspect, the conductors may be formed by processing a conductive layer into a pattern using a laser and/or mask techniques.

The reagent composition or compositions used to form the electrodes may be deposited in solid, semi-solid, liquid, gel, gellular, colloidal, or other form and may include reagents and optionally a binder. The reagent compositions may have viscosities ranging from about 1 cp to about 100 cp. More preferable reagent compositions have viscosities ranging from about 1 cp to about 20 cp or from about 4 cp to about 10 cp. Reagent compositions with other viscosities may be used. Viscosities were determined with a Brookfield Model DV3 Viscometer equipped with an ULA assembly for measuring reagent compositions having viscosities lower than 300 cp. Viscosity measurements were performed at room temperature with the instrument temperature set to 25° C. The measurements were performed at shear rates of 50, 100, 200 and 300 cps (cycle per second) to provide an indication of whether the composition is sheared thin or thick. A 100 mM phosphate buffer solution was used as a control, which typically gave viscosity readings in the range of about 1 to about 1.3 cp under different shear rates.

The binder is preferably a polymeric material that is at least partially water-soluble. The binder may form a gel or gel-like material when hydrated. Suitable partially water-soluble polymeric materials for use as the binder may include poly(ethylene oxide) (PEO), carboxy methyl cellulose (CMC), polyvinyl alcohol (PVA), hydroxyethylene cellulose (HEC), hydroxypropyl cellulose (HPC), methyl cellulose, ethyl cellulose, ethyl hydroxyethyl cellulose, carboxymethyl ethyl cellulose, polyvinyl pyrrolidone (PVP), polyamino acids, such as polylysine, polystyrene sulfonate, gelatin and derivatives thereof, polyacrylic acid and derivatives and salts thereof, polymethacrylic acid and derivatives and salts thereof, starch and derivatives thereof, maleic anhydrides and salts thereof, agarose based gels and derivatives thereof. The binder may include one or more of these materials in combination. Among the above binder materials, PEO, PVA, CMC, and HEC are preferred, with CMC being more preferred at present for biosensors. Other binders may be used.

Binders having molecular weights from 10,000 to 900,000, and preferably from 30,000 to 300,000 (weight/average) are preferred. Binders having other molecular weights may be used. Molecular weights may be determined by size exclusion chromatography (SEC), and are generally expressed as weight averages or number averages.

The reagent composition used to form the working electrode preferably includes a biomolecule responsive to the analyte of interest. Biomolecules may include active enzyme systems, such as oxidoreductases. Biomolecules also may include biopolymers, such as nucleic acids, proteins, and peptides. Other biomolecules may be used.

Oxidoreductases catalyze the transfer of electrons and facilitate the oxidation or reduction of the analyte and include "oxidases," which facilitate oxidation reactions where molecular oxygen is the electron acceptor; "reductases," which facilitate reduction reactions where the analyte is reduced and molecular oxygen is not the analyte; and "dehydrogenases," which facilitate oxidation reactions in which molecular oxygen is not the electron acceptor. See, for example, *Oxford Dictionary of Biochemistry and Molecular Biology, Revised Edition*, A. D. Smith, Ed., New York: Oxford University Press (1997) pp. 161, 476, 477, and 560. For example, Table I, below, provides oxidoreductases useful in the analysis of the listed analytes.

TABLE I

| Oxidoreductase | Analyte |
|---|---|
| Glucose dehydrogenase | β-glucose |
| Glucose oxidase | β-glucose |
| Cholesterol esterase; cholesterol oxidase | Cholesterol |
| Lipoprotein lipase; glycerol kinase; glycerol-3-phosphate oxidase | Triglycerides |
| Lactate oxidase; lactate dehydrogenase; diaphorase | Lactate |
| Pyruvate oxidase | Pyruvate |
| Alcohol oxidase | Alcohol |
| Bilirubin oxidase | Bilirubin |
| Uricase | Uric acid |
| Glutathione reductase | NAD(P)H |
| Carbon monoxide oxidoreductase | Carbon monoxide |

The biomolecules may include amine functional groups capable of hydrogen bonding interactions. Biomolecules having weight/average molecular weights from 10,000 to 500,000 and preferably from 100,000 to 400,000 that maintain biological activity after deposition are preferred. In the case of oxidoreductases, from 0.01 to 100 Units (U), preferably from 0.05 to 10 U, and more preferably from 0.1 to 5 U may be used per test sensor or analysis. In another aspect, at most 1.3 U of the oxidoreductase is used.

The reagent layer formed from depositing the reagent composition on the conductor may include an enzyme system specific to the analyte that may facilitate the reaction of the analyte while enhancing the specificity of the sensor system to the analyte, especially in complex biological samples. The enzyme system may include one or more enzyme, cofactor, and/or other moiety that participates in the redox reaction with the analyte. For example, an alcohol oxidase can be used to provide a biosensor that is sensitive to the presence of alcohol in a sample. Such a system could be useful in measuring blood alcohol concentrations. In another example, glucose dehydrogenase or glucose oxidase may be used to provide a biosensor that is sensitive to the presence of glucose in a sample. This system could be useful in measuring blood glucose concentrations, for example in patients known or suspected to have diabetes.

Preferable enzyme systems are oxygen independent, thus not substantially oxidized by oxygen. One such oxygen independent enzyme family is glucose dehydrogenase (GDH). Using different co-enzymes or co-factors, GDH may be mediated in a different manner by different mediators. Depending on their association with GDH, a co-factor, such as flavin adenine dinucleotide (FAD), can be tightly held by the host enzyme, such as in the case of FAD-GDH; or a co-factor, such as Pyrroloquinolinequinone (PQQ), may be covalently linked to the host enzyme, such as with PQQ-GDH. The co-factor in each of these enzyme systems may either be permanently held by the host enzyme or the co-enzyme and the apoenzyme may be re-constituted before the enzyme system is added to the reagent composition. The co-enzyme also may be independently added to the host enzyme moiety in the reagent composition to assist in the catalytic function of the host enzyme, such as in the cases of nicotinamide adenine dinucleotide NAD/NADH$^+$ or nicotinamide adenine dinucleotide phosphate NADP/NADPH$^+$. Other useful dehydrogenase enzyme systems include alcohol dehydrogenase, lactate dehydrogenase, β-hydroxybutyrate dehydrogenase, glucose-6-phosphate dehydrogenase, glucose dehydrogenase, formaldehyde dehydrogenase, malate dehydrogenase, and 3-hydroxysteroid dehydrogenase.

The reagent layer also may include a mediator to communicate the results of the analyte reaction to the conductor. Mediators may be oxidized or reduced and may transfer one or more electrons. A mediator is a reagent in an electrochemical analysis and is not the analyte of interest, but provides for the indirect measurement of the analyte. In a simple system, the mediator undergoes a redox reaction in response to the oxidation or reduction of the analyte. The oxidized or reduced mediator then undergoes the opposite reaction at the working electrode of the test sensor and may be regenerated to its original oxidation number. Thus, the mediator may facilitate the transfer of electrons from the analyte to the working electrode.

Figure 9A:
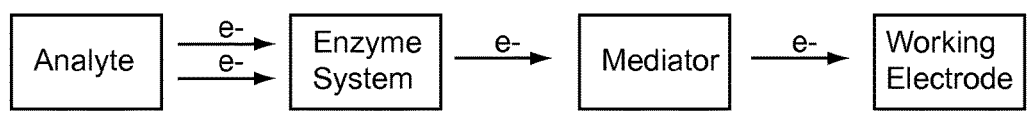
FIG. 9A represents a one electron transfer mediator transferring one electron.
Figure 9B:
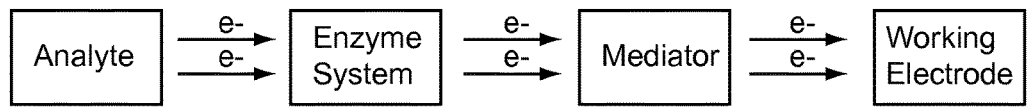
FIG. 9B represents a multi-electron transfer mediator transferring two electrons.

Mediators may be separated into two groups based on their electrochemical activity. One electron transfer mediators are chemical moieties capable of taking on one additional electron during the conditions of the electrochemical reaction. Multi-electron transfer mediators are chemical moieties capable of taking on more-than-one electron during the conditions of the reaction. As depicted in FIG. 9A, one electron transfer mediators can transfer one electron from the enzyme to the working electrode, while as depicted in FIG. 9B, a multi-electron transfer mediator can transfer two electrons.

Examples of one electron transfer mediators include compounds, such as 1,1'-dimethyl ferrocene, ferrocyanide and ferricyanide, and ruthenium(III) and ruthenium(II) hexaamine. Two electron mediators include the organic quinones and hydroquinones, such as phenanthroline quinone; phenothiazine and phenoxazine derivatives; 3-(phenylamino)-3H-phenoxazines; phenothiazines; and 7-hydroxy-9,9-dimethyl-9H-acridin-2-one and its derivatives. Examples of additional two electron mediators include the electro-active organic molecules described in U.S. Pat. Nos. 5,393,615; 5,498,542; and 5,520,786, which are incorporated herein by reference, for example.

Preferred two electron transfer mediators include 3-phenylimino-3H-phenothiazines (PIPT) and 3-phenylimino-3H-phenoxazines (PIPO). More preferred two electron mediators include the carboxylic acid or salt, such as ammonium salts, of phenothiazine derivatives. At present, especially preferred two electron mediators include (E)-2-(3H-phenothiazine-3-ylideneamino)benzene-1,4-disulfonic acid (Structure I), (E)-5-(3H-phenothiazine-3-ylideneamino) isophthalic acid (Structure II), ammonium (E)-3-(3H-phenothiazine-3-ylideneamino)-5-carboxybenzoate (Structure III), and combinations thereof. The structural formulas of these mediators are presented below. While only the di-acid form of the Structure I mediator is shown, mono- and di-alkali metal salts of the acid are included. At present, the sodium salt of the acid is preferred for the Structure I mediator. Alkali-metal salts of the Structure II mediator also may be used.

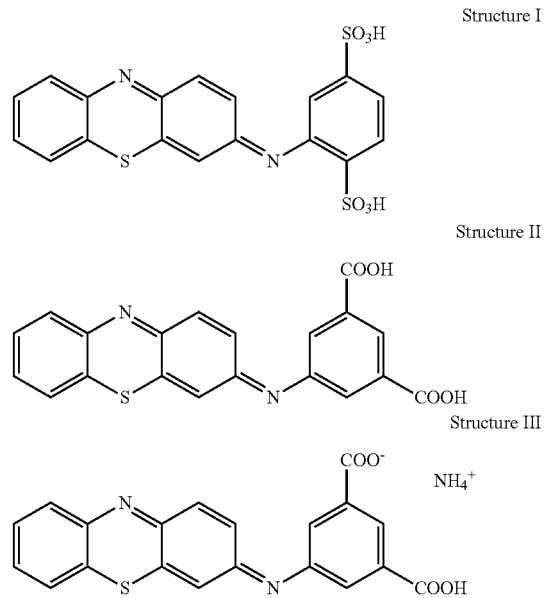

In another respect, preferred two electron mediators have a redox potential that is at least 100 mV lower, more preferably at least 150 mV lower, than ferricyanide.

The charge transfer system is any one or a combination of electrochemically active species that may transfer one or more electrons from or to a counter electrode. For example, if the working electrode of a system transfers electrons to a counter electrode through the measurement device, the charge transfer system of the counter electrode accepts electrons from the counter electrode to allow the measurement of current flow through the system. By accepting electrons at a specific potential or potential range, the charge transfer system influences the potential at which the working electrode may transfer electrons for measurement. The charge transfer system may or may not include the mediator present at the working electrode; but if it does, at least a portion of the mediator at the counter electrode preferably has an oxidation state different than the mediator at the working electrode.

Because the electrochemical reaction with the lowest potential will occur first, by providing the working electrodes with one or more analyte responsive biomolecule, such as an oxidoreductase, and/or mediators that transport charge at increasing potentials, the electrochemistry of multiple working electrodes may be sequentially analyzed from lowest to highest operating potential. If the working and counter electrodes may be independently addressed, a working electrode having a specific redox potential with an analyte can be selectively paired with a counter electrode having the desired potential. If the redox potentials of the analyte, analyte responsive biomolecule, and/or mediator at independently addressable working electrodes are different, separate output signals for individual analysis may be measured when using electrically connected counter electrodes. Conversely, if the redox potentials of the charge transfer species at independently addressable counter electrodes are different, separate output signals for individual analysis may be measured when using electrically connected working electrodes. When multiple counter electrodes have different charge transfer species but are electrically connected, the counter electrode having the highest potential will provide the operating potential to the working electrode until the system potential drops to that of the next highest potential counter electrode.

Figure 10A:
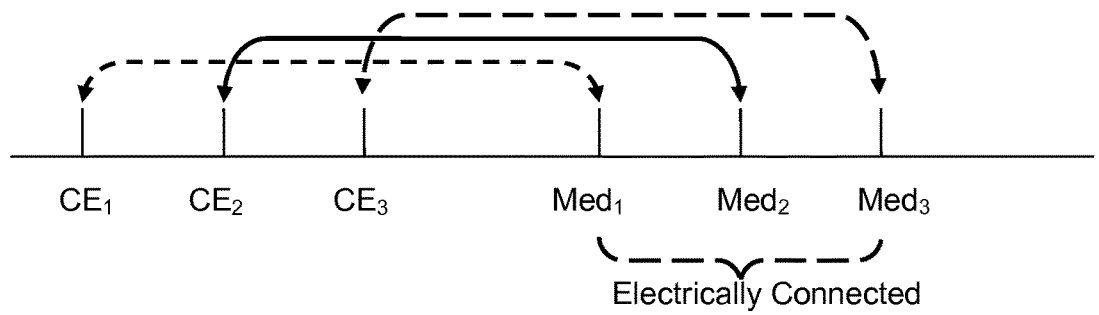
FIG. 10A represents a system having three independently addressable counter electrodes, each operating at a different potential, and three electrically connected working electrodes, each having a mediator system that operates at a different potential.

FIG. 10A represents a system having three independently addressable counter electrodes ($CE_1$-$CE_3$), each operating at a different potential, and three electrically connected working electrodes, each having a mediator system that operates at a different potential. As the operating potential of the system is increased at counter electrodes $CE_1$ through $CE_3$, the redox characteristics of mediators ($Med_1$-$Med_3$) at the electrically connected working electrodes may be independently measured. For instance, when $CE_1$ is coupled with the working electrode, $Med_1$ reacts at the electrode. When $CE_2$ is coupled with the working electrode, $Med_1$ and $Med_2$ react at the electrode. Finally, when $CE_3$ is coupled with the working electrode, all three mediator systems may react at the working electrode.

Figure 10B:
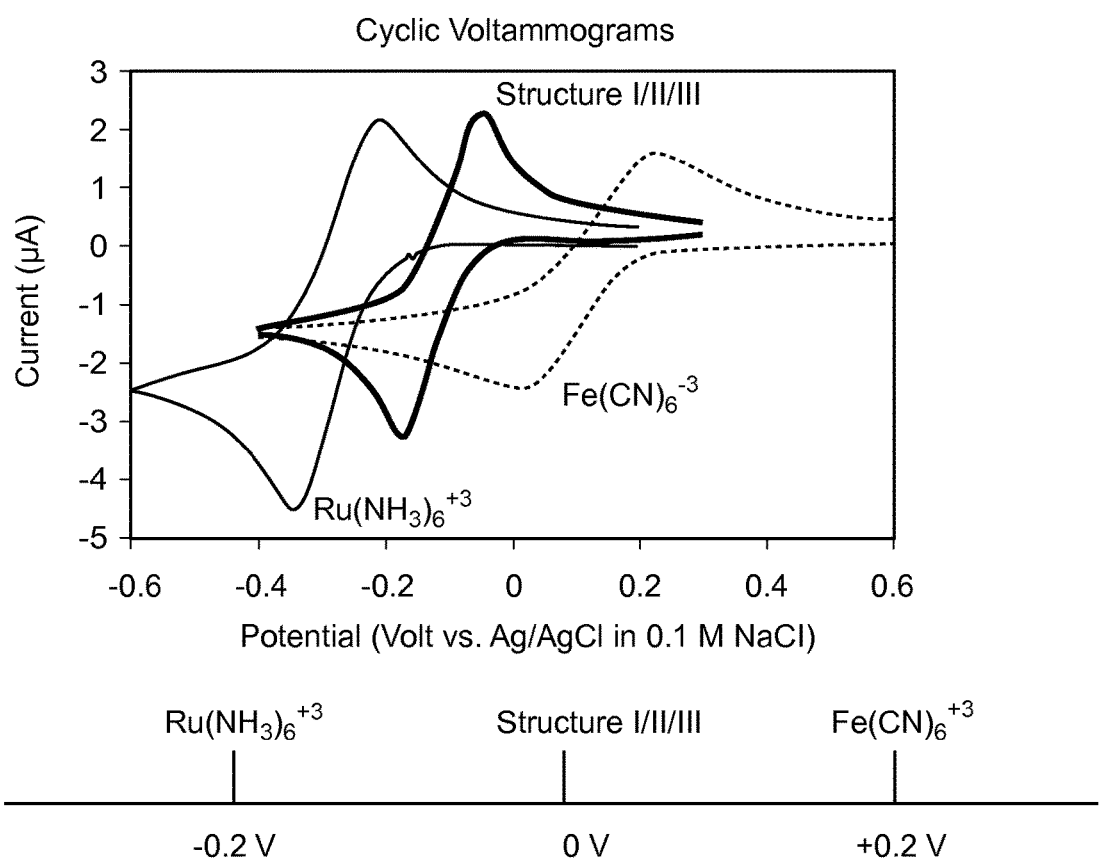
FIG. 10B shows cyclic voltammograms of ruthenium(III) hexaamine, ferricyanide, and an electro-active organic molecule.

Multiple operating potentials may be provided to the system by altering the charge transfer system deposited on different conductors to form counter electrodes. The potential provided by a specific counter electrode may be altered with charge transfer systems including different redox species (moieties that may be oxidized and/or reduced) and/or different ratios of the redox conjugate pairs (reduced and oxidized moieties of the same redox species) of a redox species, such as ferrocyanide/ferricyanide. Examples of different redox species for use in charge transfer systems include soluble or insoluble redox species, where soluble redox species are soluble in water (pH 7, 25° C.) at a level of at least 1.0 grams per Liter and exclude elemental metals and lone metal ions that are insoluble or sparingly soluble in water. Useful redox species include electro-active organic molecules, organotransition metal complexes, and transition metal coordination complexes. Unlike metal containing organotransition metal complexes and coordination complexes, electro-active organic molecules lack a metal capable of undergoing oxidation or reduction. Preferable redox species for use in charge transfer systems include ruthenium(III) hexaamine, ferricyanide, and electro-active organic molecules, such as PIPT and PIPO. FIG. 10B shows cyclic voltammograms of the ruthenium(III) hexaamine, ferricyanide, and the electro-active organic molecule represented above in Structure I/II/III. As seen in the graph, the relative potential positions of each redox species are separated by about 200 mV.

Examples of different ratios of redox conjugate pairs are the ratio of ferrocyanide to ferricyanide in the charge transfer system. For example, a ratio of 9.5:0.5 may be used for the lowest potential counter electrode, while ratios of 8:2, 5:5, 2:8, and 0.5:9.5 may be used to provide counter electrodes having progressively increasing operating potentials. Pure ferricyanide may be used to provide a counter electrode having the highest operating potential for the six counter electrodes. In this manner, six independently addressable counter electrodes may be formed using different ratios of redox conjugate pairs, each providing a different potential to the system. Thus, potential differences less than those obtainable with different redox species, such as at least 50 mV, or at least 100 mV, may be obtained using different ratios of the conjugate pairs of a redox species.

Figure 10C:
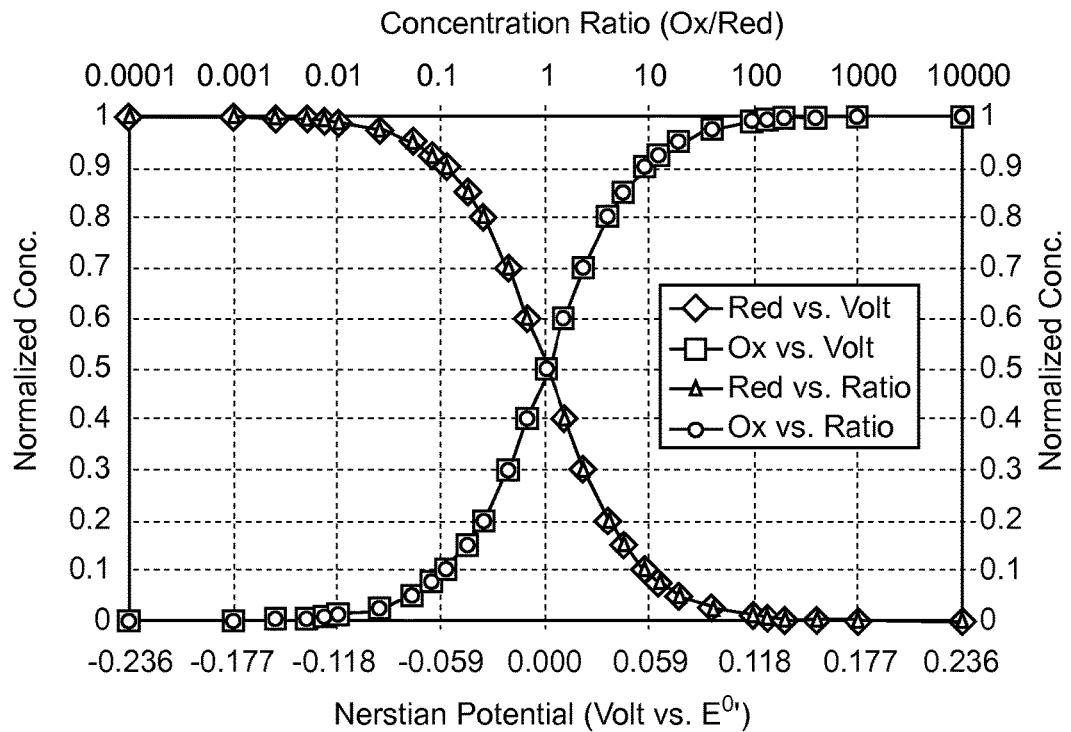
FIG. 10C is a graph relating counter electrode operating potential and redox conjugate pair ratio.

The relationship of counter electrode operating potential vs. redox conjugate pair ratio is characterized by the Nernst equation and is shown in FIG. 10C. Depending on whether oxidation or reduction is occurring at the counter electrode during analysis, the desired potential can be provided to the counter electrode by selecting the appropriate redox conjugate pair ratio for the deposited charge transfer system. By selecting different ratios of the redox conjugate pairs for the charge transfer systems, the potential of the charge transfer system may be varied by about ±150 mV for different ratios of ferrocyanide/ferricyanide. Thus, in addition to the use of different redox species to provide different operating potentials to multiple counter electrodes, different ratios of the conjugates of the redox species may be used. Substantial chemical isolation, as may be provided by the physical separation between the secondary regions, allows the different charge transfer systems of each counter electrode to provide different operating potentials to the system during the analysis.

Figure 10D:
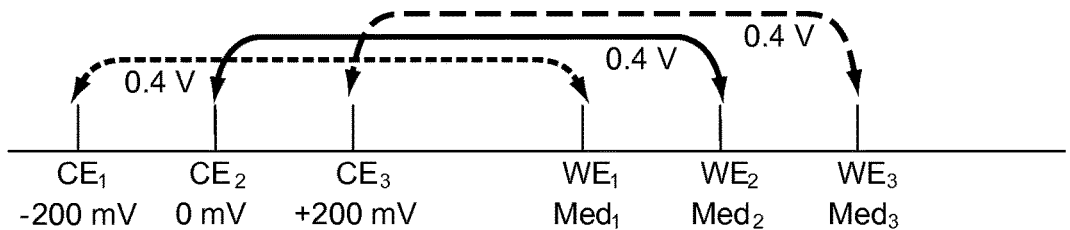
FIG. 10D represents the charge transfer systems of multiple independently addressable counter electrodes.

FIG. 10D represents the circumstance where the charge transfer systems of multiple independently addressable counter electrodes ($CE_1$-$CE_3$) provide different absolute operating potentials, such as −200 mV, 0 mV, and +200 mV, while maintaining substantially the same relative operating potential of 0.4 V between the counter and working electrodes. The center redox couple arbitrarily may be assigned a fixed potential of zero against a Standard Hydrogen Electrode, a Saturated Calomel Electrode, or the like. Thus, ruthenium hexaamine has a redox potential that is about 200 mV lower and ferricyanide has a redox potential that is about 200 mV higher than that of the Structure I/II/III molecule. By operating the counter electrodes at different absolute operating potentials in relation to a known potential, the system may independently analyze the different mediator systems ($Med_1$-$Med_3$) at the electrically connected working electrodes $WE_1$ through $WE_3$.

Figure 10E:
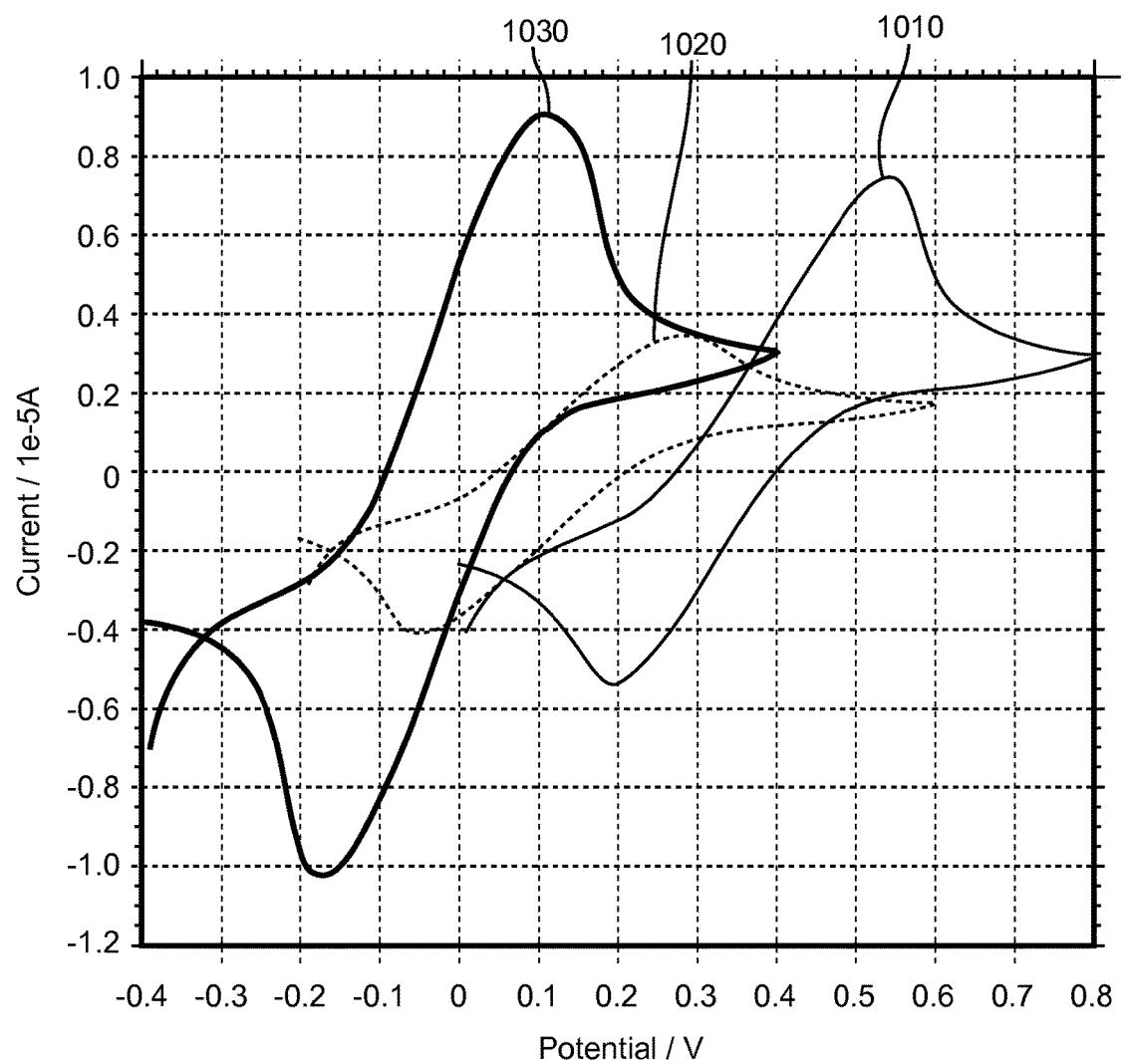
FIG. 10E shows cyclic voltammograms establishing the different operating potentials that may be provided to one or more working electrodes by multiple independently addressable counter electrodes.

FIG. 10E shows cyclic voltammograms establishing the different operating potentials that may be provided to one or more working electrodes by multiple independently addressable counter electrodes. A test sensor having a multi-T design with eight secondary analysis regions was fabricated, such as previously depicted in FIG. 3I. Four of the secondary analysis regions were provided with independently addressable working electrodes and four of the secondary analysis regions were provided with independently addressable counter electrodes. Each working electrode was formed with a reagent composition including 0.5% weight/weight (w/w) HEC binder, 50 mM of the Structure I molecule, and 2 U/μL of the PQQ-GDH enzyme system in a phosphate buffer of pH 7. The first counter electrode was formed with a charge transfer system including 0.5% (w/w) HEC binder and 100 mM ruthenium hexaamine in phosphate buffer of pH 7. The second counter electrode was formed with a charge transfer system including 0.5% (w/w) HEC binder and 100 mM of the Structure I molecule in phosphate buffer of pH 7. The third and fourth counter electrodes were formed with a charge transfer system including 0.5% (w/w) HEC binder and 100 mM ferricyanide in phosphate buffer of pH 7.

After introduction of a sample including 300 mg/dL of glucose, the CH Instrument was scanned at a rate of 25 mV/sec for one of the working electrodes and each of the first, second, and third counter electrodes. As shown in FIG. 10E, the potential of the ruthenium hexaamine counter electrode, line 1010, peaks at a potential about 400 mV higher than ferricyanide, line 1030, with the Structure I molecule peaking approximately in the middle, line 1020. In this manner, the results observed for the in the cyclic voltammograms of 10E were reproduced in a multi-T test sensor design having multiple secondary analysis regions. Thus, the ability of the test sensor to operate at multiple potentials using multiple counter electrodes with different charge transfer systems was demonstrated.

Figure 11A:
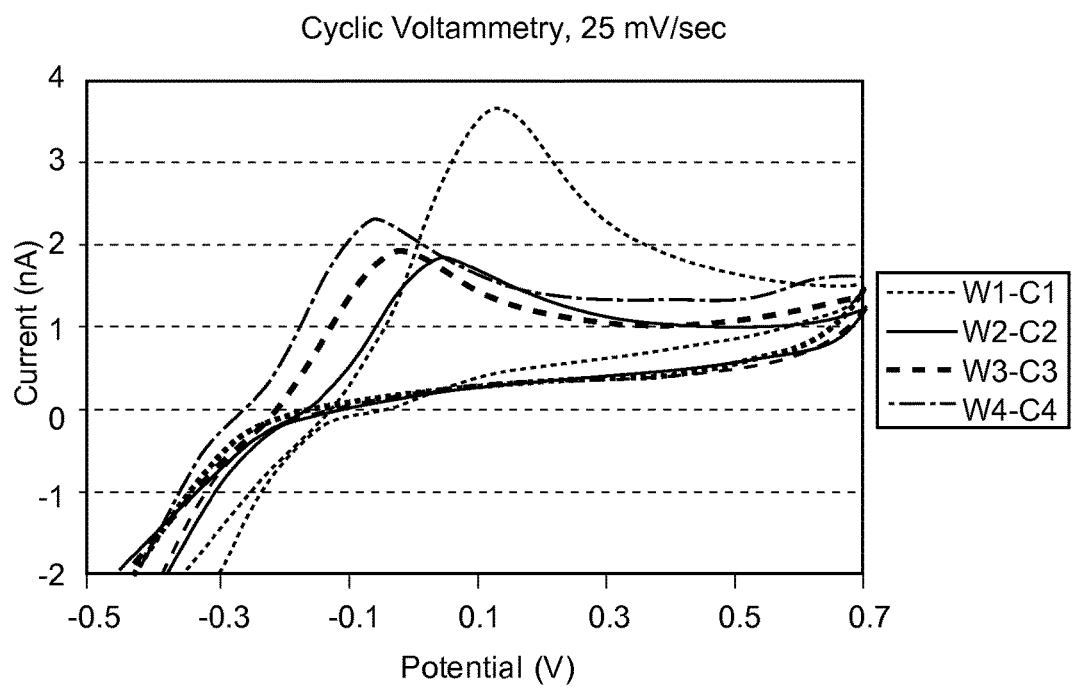
FIG. 11A establish that the charge transfer systems of FIG. 10E may be replaced with multiple redox conjugate pair ratios to provide multiple potentials to the system.

FIG. 11A establishes that the charge transfer systems of FIG. 10E may be replaced with multiple redox conjugate pair ratios to provide multiple potentials to the system. A test sensor was prepared as in FIG. 10E, but the first counter electrode was formed with a charge transfer system including 0.5% (w/w) HEC binder and a 1:9 ratio of ferricyanide:ferrocyanide 200 mM in phosphate buffer of pH 7, the second counter electrode was formed with a charge transfer system including 0.5% (w/w) HEC binder and a 1:1 ratio of ferricyanide:ferrocyanide 200 mM in phosphate buffer of pH 7, the third counter electrode was formed with a charge transfer system including 0.5% (w/w) HEC binder and a 9:1 ratio of ferricyanide:ferrocyanide 200 mM in a phosphate buffer of pH 7, and the fourth counter electrode was formed with a charge transfer system including 0.5% (w/w) HEC binder and substantially pure ferricyanide 200 mM in phosphate buffer of pH 7.

After introduction of a sample including 300 mg/dL of glucose, the instrument was scanned at a rate of 25 mV/sec for one of the working electrodes and each of the first, second, third, and fourth counter electrodes. FIG. 11A showed the first counter electrode to have a peak potential of about 0.149 V (W1-C1), the second counter electrode to have a peak potential of about 0.060 V (W2-C2), the third counter electrode to have a peak potential of about −0.007 V (W3-C3), and the fourth counter electrode to have a peak potential of about −0.047 V (W4-C4). Thus, the ability of the test sensor to operate at multiple potentials using multiple counter electrodes with charge transfer systems relying on different ratios of a redox conjugate pair was demonstrated.

Figure 11B:
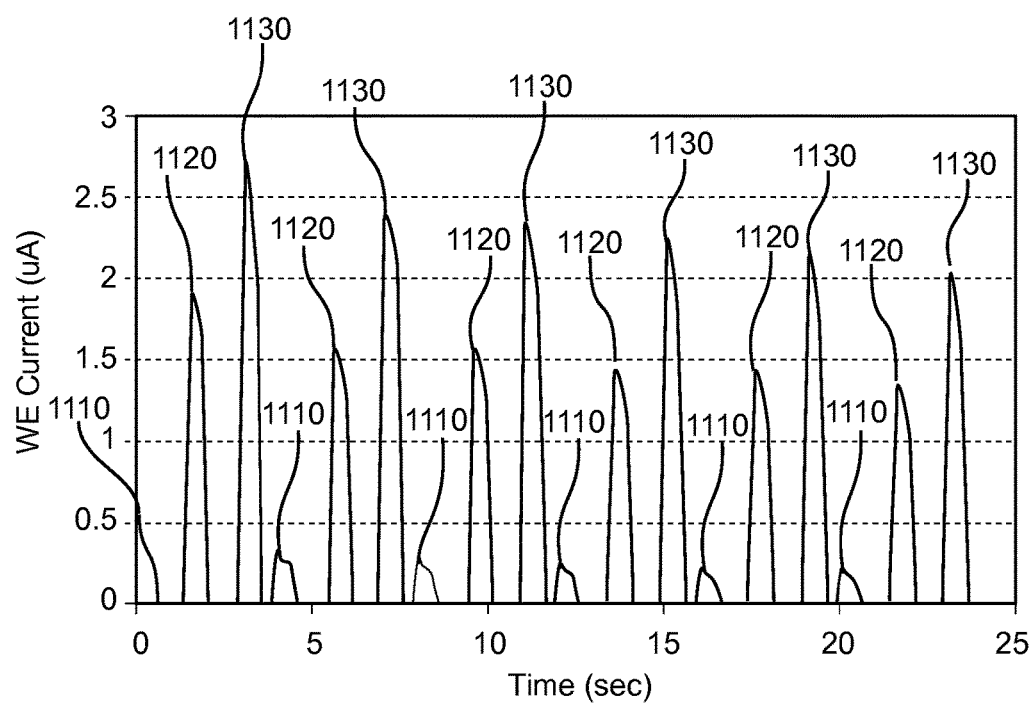
FIG. 11B depicts the current profiles obtained when the potential at one substantially chemically isolated working electrode is repetitively controlled in sequence by three substantially chemically isolated and independently addressable counter electrodes, each having a different potential provided by different charge transfer systems.

FIG. 11B depicts the current profiles obtained when the potential at one substantially chemically isolated working electrode is repetitively controlled in sequence by three substantially chemically isolated and independently addressable counter electrodes, each having a different potential provided by different charge transfer systems. A test sensor was prepared as in FIG. 10E, but the multiple working electrodes were replaced with a single working electrode. A first peak 1110 in each of the six series of three peaks was obtained from the first counter electrode, a second peak 1120 in each of the six series of three peaks was obtained from the second counter electrode, and a third peak 1130 in each of the six series of three peaks was obtained from the third counter electrode. The first peaks 1110 demonstrated the current level obtained from using ruthenium hexamine as the charge transfer system at the first counter electrode. The second peaks 1120 demonstrated the current level obtained from using the Structure I molecule as the charge transfer system at the second counter electrode. The third peaks 1130 demonstrated the current level obtained from using ferricyanide as the charge transfer system at the third counter electrode. In this manner, for the same potential different counter electrode potentials will address different oxidation points of the same oxidation wave. Thus, in addition to demonstrating the ability of the multiple counter electrodes to control the operating potential at the working electrode, the ability of the system to conduct three separate analyses at the working electrode with a gated input signal was established.

Figure 12A:
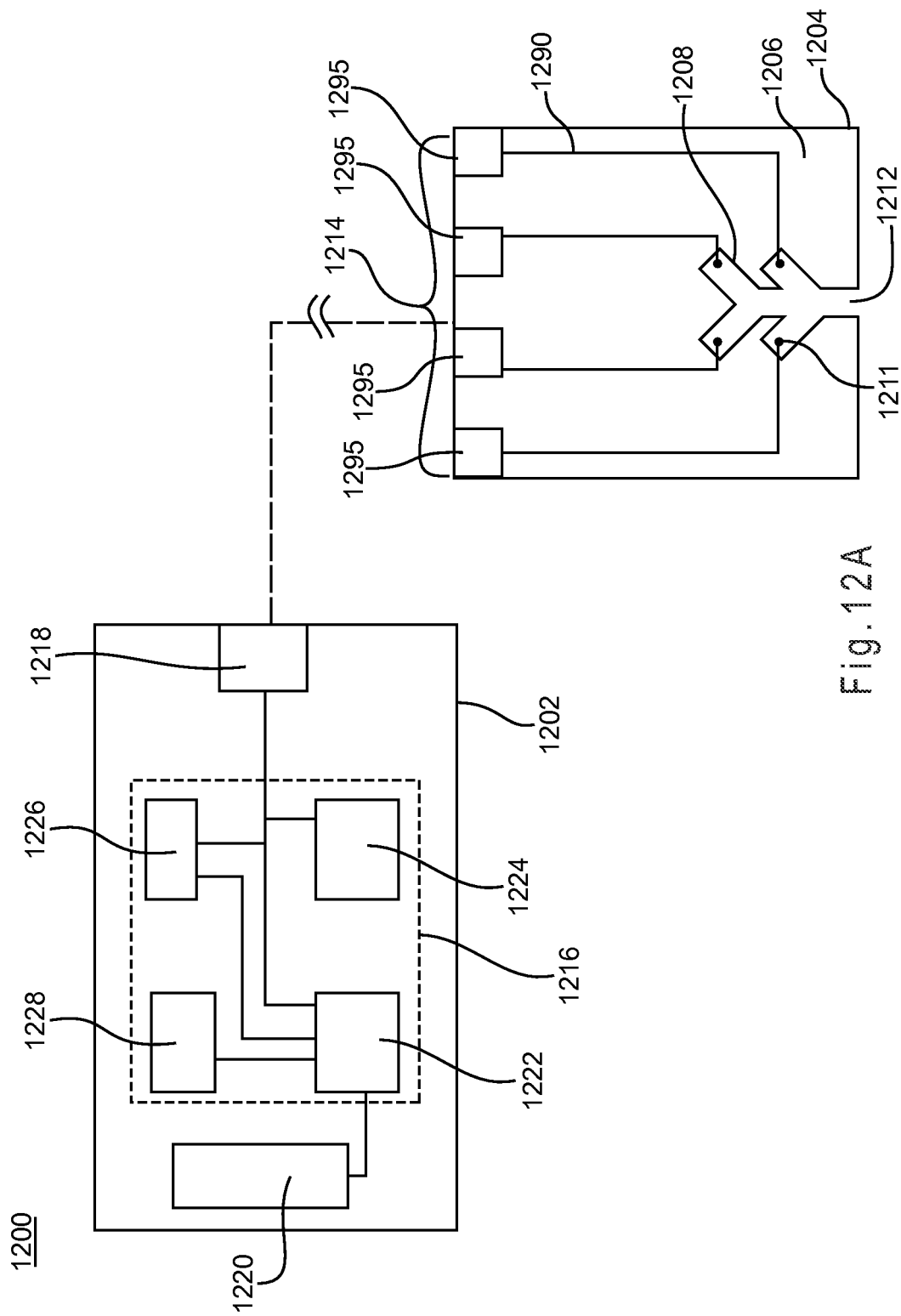
FIG. 12A depicts a schematic representation of a biosensor system that determines an analyte concentration in a sample of a biological fluid.

FIG. 12A depicts a schematic representation of a biosensor system 1200 that determines an analyte concentration in a sample of a biological fluid using an input signal. Biosensor system 1200 includes a measurement device 1202 and a test sensor 1204, which may be implemented in an analytical instrument, including a bench-top device, a portable or hand-held device, or the like. The biosensor system 1200 may be utilized to determine analyte concentrations, including those of glucose, uric acid, lactate, cholesterol, bilirubin, and the like.

While a particular configuration is shown, the biosensor system 1200 may have other configurations, including those with additional components. For example, the test sensor 1204 may be adapted for use outside, inside, or partially inside a living organism. When used outside a living organism, a sample of the biological fluid is introduced into a sample reservoir in the test sensor 1204. The test sensor 1204 may be placed in the measurement device before, after, or during the introduction of the sample for analysis. When inside or partially inside a living organism, a test sensor may be continually immersed in the sample or the sample may be intermittently introduced to the sensor.

The test sensor 1204 has a base 1206 that forms a reservoir 1208 with an opening 1212. The reservoir 1208 may be formed by a lid with a vent. The reservoir 1208 defines a partially-enclosed volume, but may be open to the sample (not shown). Thus, the sample may continuously flow through the test sensor or be interrupted for analysis.

The reservoir 1208 may contain a composition that assists in retaining a liquid sample such as water-swellable polymers or porous polymer matrices. Reagents may be deposited in the reservoir 1208. The reagents may include one or more enzymes, enzyme systems, mediators, binders, and like species. The binder may include various types and molecular weights of polymers, such as HEC (hydroxy ethyl cellulose), (CMC (carboxyl methyl cellulose), and/or PEO (polyethylene oxide). In addition to binding the reagents together, the binder may assist in filtering red blood cells, preventing them from coating the electrode surfaces 1211. The test sensor 1204 also may have a sample interface 1214 disposed adjacent to the reservoir 1208. The sample interface 1214 may partially or completely surround the reservoir 1208. The test sensor 1204 may have other configurations. For example, the test sensor 1204 may be adapted for transdermal use by forming the reservoir 1208 from a porous material or behind a porous material in which the sample is held.

The sample interface 1214 has conductors 1290 connected to at least one working electrode and at least two counter electrodes. The electrodes may be substantially in the same plane or in more than one plane, such as when facing. The electrodes may be disposed on a surface of the base 1206 that forms the reservoir 1208. The electrodes may extend or project into the reservoir 1208. One or more of the conductors 1290 also may extend into the reservoir 1208 to provide functionality not provided by the electrodes. A dielectric layer may partially cover the conductors and/or the electrodes. The counter electrodes may be used to balance the potential at one or more working electrode during the analysis. The balancing potential may be provided by forming the counter electrode from an inert material, such as carbon, and including a soluble redox species, such as ferricyanide, within the reservoir 1208. Alternatively, the balancing potential may be a reference potential achieved by forming the counter electrode from a reference redox couple, such as Ag/AgCl, to provide a combined reference-counter electrode. The sample interface 1214 may have other electrodes and conductors.

The measurement device 1202 includes electrical circuitry 1216 connected to a sensor interface 1218 and a display 1220. The electrical circuitry 1216 includes a processor 1222 connected to a signal generator 1224, an optional temperature sensor 1226, and a storage medium 1228.

The signal generator 1224 provides an electrical input signal to the sensor interface 1218 in response to the processor 1222. The electrical input signal may be transmitted by the sensor interface 1218 to the sample interface 1214 to apply the electrical input signal to the sample of the biological fluid. The electrical input signal may be transmitted through all or a portion of the conductors 1290 at the sample interface 1214. The electrical input signal may be a potential or current and may be constant, variable, or a combination thereof, such as when an AC signal is applied with a DC signal offset. The electrical input signal may be applied as a single pulse or in multiple pulses, sequences, or cycles. The signal generator 1224 also may record an output signal from the sensor interface as a generator-recorder.

Figure 12B:
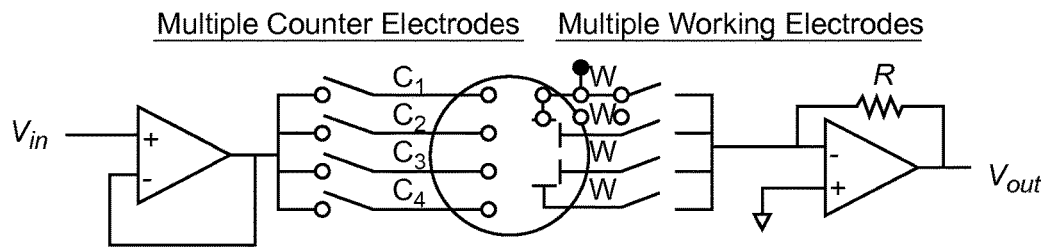
FIG. 12B through FIG. 12F represent multiple potentiostat variations that may be used with the signal generator of FIG. 12A.
Figure 12C:
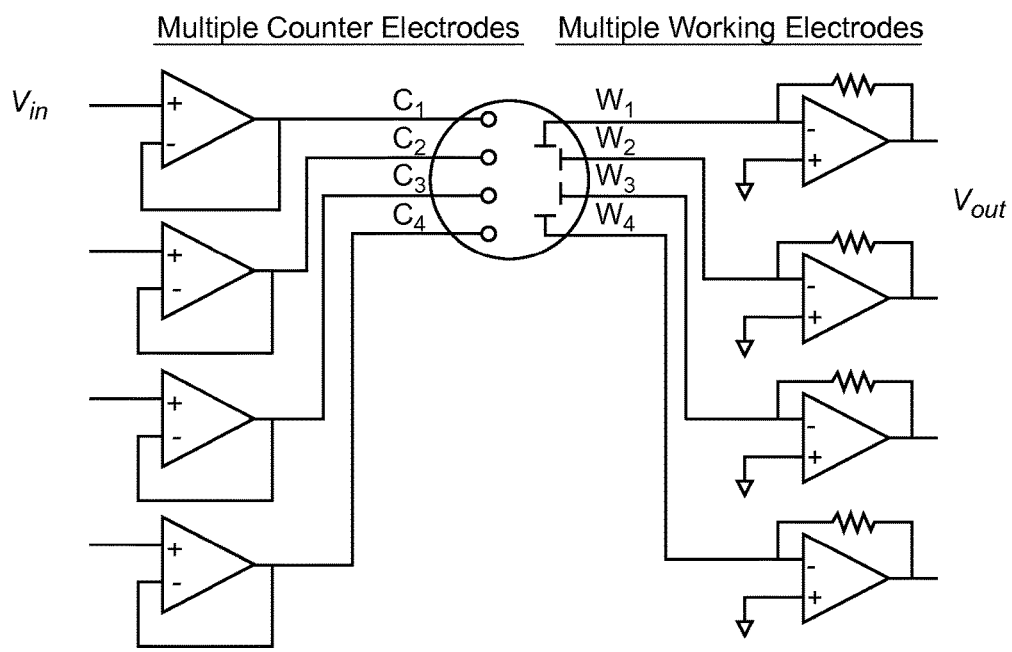
Figure 12D:
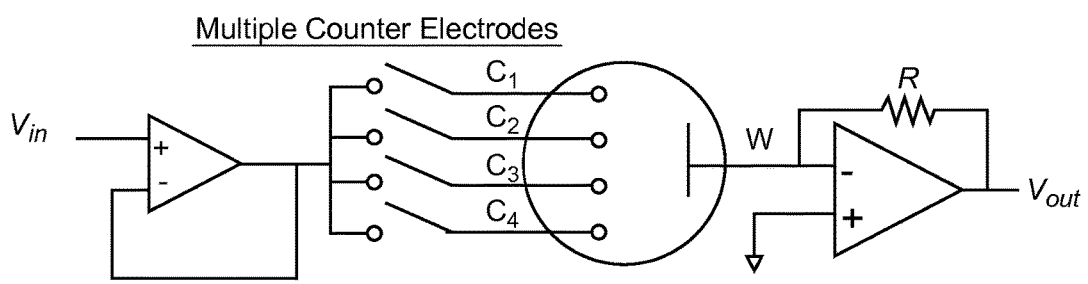
Figure 12E:
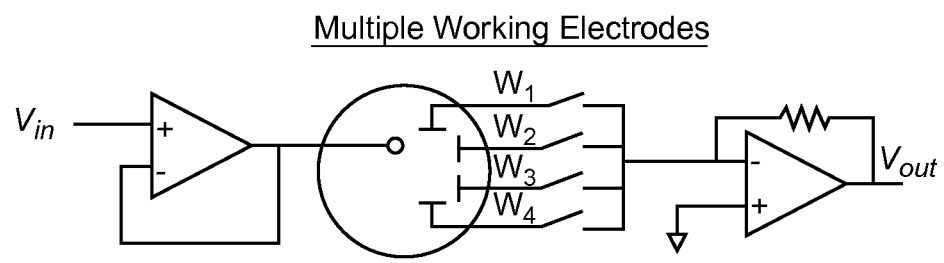
Figure 12F:
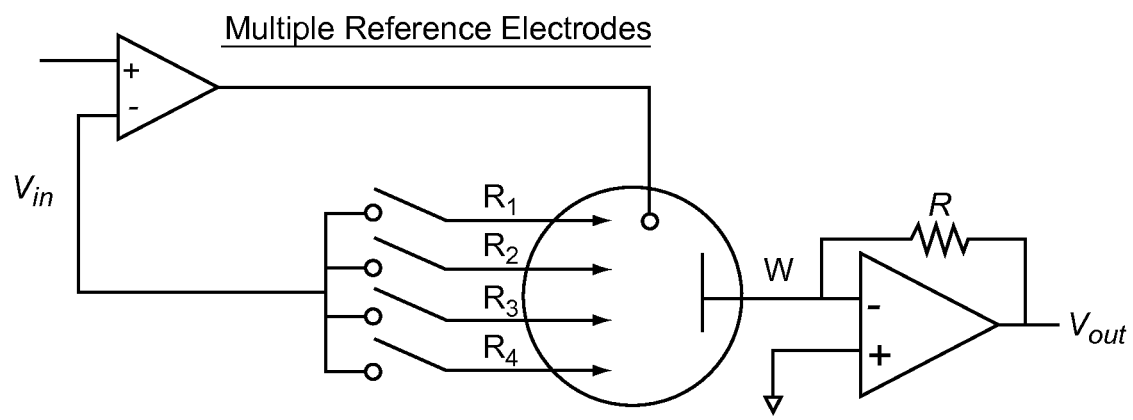

The signal generator 1224 may include the potentiostat of FIG. 12B, which may switch between multiple independently addressable working and counter electrodes, or may include the multiple potentiostat system of FIG. 12C. FIG. 12D represents a potentiostat that may be implemented in the signal generator to switch between four counter electrodes and an electrically connected working electrode. FIG. 12E represents a potentiostat implemented to switch between four working electrodes and an electrically connected counter electrode. FIG. 12F represents a potentiostat implemented to switch between four reference electrodes and an electrically connected working electrode. The one or more potentiostats may provide different operating potentials to the sample interface 1214. The signal generator 1224 may be configured where a function generator triggers gated wave inputs to the potentiostat. The signal generator 1224 may have other configurations.

The optional temperature sensor 1226 determines the temperature of the sample in the reservoir of the test sensor 1204. The temperature of the sample may be measured, calculated from the output signal, or presumed to be the same or similar to a measurement of the ambient temperature or the temperature of a device implementing the biosensor system. The temperature may be measured using a thermister, thermometer, or other temperature sensing device. Other techniques may be used to determine the sample temperature.

The storage medium 1228 may be a magnetic, optical, or semiconductor memory, another storage device, or the like. The storage medium 1228 may be a fixed memory device, a removable memory device, such as a memory card, remotely accessed, or the like.

The processor 1222 implements the analyte analysis and data treatment using computer readable software code and data stored in the storage medium 1228. The processor 1222 may start the analyte analysis in response to the presence of the test sensor 1204 at the sensor interface 1218, the application of a sample to the test sensor 1204, in response to user input, or the like. The processor 1222 directs the signal generator 1224 to provide the electrical input signal to the sensor interface 1218. The processor 1222 may receive the sample temperature from the optional temperature sensor 1226.

The processor 1222 receives the output signal from the sensor interface 1218. The output signal is generated in response to the redox reaction of the measurable species in the sample. The electrical output signal from the test sensor may be a current (as generated by amperometry or voltammetry), a potential (as generated by potentiometry/galvanometry), or an accumulated charge (as generated by coulometry). The output signal is correlated with the concentration of one or more analytes in the sample using one or more correlation equations in the processor 1222. The results of the analyte analysis may be output to the display 1220 and may be stored in the storage medium 1228.

The correlation equations between analyte concentrations and output signals may be represented graphically, mathematically, a combination thereof, or the like. The correlation equations may be represented by a program number (PNA) table, another look-up table, or the like that is stored in the storage medium 1228. Instructions regarding implementation of the analyte analysis may be provided by the computer readable software code stored in the storage medium 1228. The code may be object code or any other code describing or controlling the functionality described herein. The data from the analyte analysis may be subjected to one or more data treatments, including the determination of decay rates, K constants, ratios, and the like in the processor 1222.

The sensor interface 1218 has contacts 1295 that connect or electrically communicate with the conductors 1290 in the sample interface 1214 of the test sensor 1204. The sensor interface 1218 transmits the electrical input signal from the signal generator 1224 through a connector in the sensor interface 1218 to the contacts 1295 in the sample interface 1214. The sensor interface 1218 also transmits the output signal from the sample through the contacts 1295 to the processor 1222 and/or signal generator 1224.

The display 1220 may be analog or digital. The display may be an LCD display adapted to displaying a numerical reading.

In use, a liquid sample for analysis is transferred into the reservoir 1208 by introducing the liquid to the sample port 1212. The liquid sample flows through the sample port 1212, filling the reservoir 1208 while expelling the previously contained air. The liquid sample chemically reacts with the reagents deposited in the secondary analysis regions of the reservoir 1208.

The test sensor 1202 is disposed adjacent to the measurement device 1202. Adjacent includes positions where the sample interface 1214 is in electrical communication with the sensor interface 1208. Electrical communication includes the transfer of input and/or output signals between contacts in the sensor interface 1218 and the conductors 1290 in the sample interface 1214.

Figure 13:
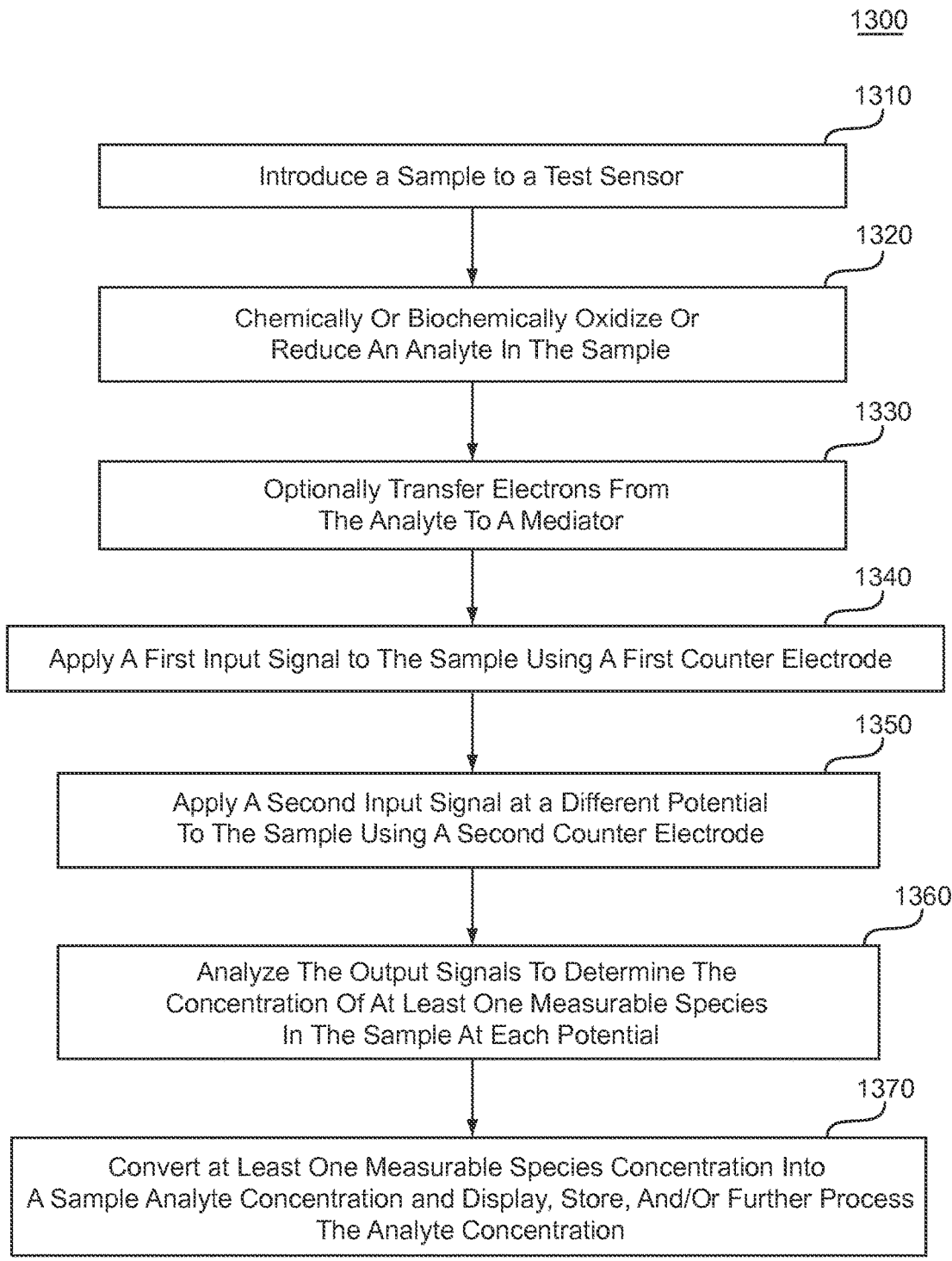
FIG. 13 represents an electrochemical analysis for determining the presence and/or concentration of at least one analyte in a sample.

FIG. 13 represents an electrochemical analysis 1300 for determining the presence and/or concentration of at least one analyte in a sample. In sample introduction 1310, the sample is introduced to the test sensor. In redox reaction 1320, a portion of the analyte in the sample undergoes a redox reaction. In electron transfer 1330, electrons are optionally transferred from the analyte to a mediator. In first input signal application 1340, an input signal is applied between a working and a first counter electrode. In second input signal application 1350, an input signal of a different potential is applied between a working and a second counter electrode. In sample determination 1350, the presence and/or concentration of one or more measurable species in the sample is determined from one or more output signals, and in sample concentration transmission 1360, the determined measurable species concentration may be displayed, stored, further processed, and the like.

In the sample introduction 1310, the sample is introduced to the sensor portion of the system, such as a test sensor. The test sensor includes at least one working and at least two counter electrodes. The electrodes may include one or more reagent composition layers. The working electrode may include a diffusion barrier layer that is integral to a reagent composition layer or that is distinct from the reagent composition layer. The diffusion barrier layer provides a porous space having an internal volume where a measurable species may reside. The pores of the diffusion barrier layer may be selected so that the measurable species may diffuse into the diffusion barrier layer, while physically larger sample constituents, such as red blood cells, are substantially excluded. When the working electrode includes a distinct diffusion barrier layer, the reagent layer may or may not be disposed on the diffusion barrier layer. Depending on the nature of the analysis 1300, the conductors may serve as electrodes. In this aspect, the reagents may be present in the sample, such as if deposited adjacent the electrodes.

In the redox reaction 1320 of FIG. 13, a portion of the analyte present in the sample is chemically or biochemically oxidized or reduced, such as by an oxidoreductase or similar species. This redox reaction occurs as the sample hydrates the reagents. Upon oxidation or reduction, electrons optionally may be transferred between the analyte and a mediator in the electron transfer 1330. Thus, an ionized measurable species is formed, such as from the analyte or a mediator, having a sample concentration responsive to the analyte. It may be beneficial to provide an initial time delay, or "incubation period," for the reagents to react with the analyte.

In the first input signal application 1340 of FIG. 13, the system applies an input signal to the sample using a first counter electrode. Input signals are electrical signals, such as current or potential, and may be a sequence of excitation pulses separated by relaxations. The system may apply one or more input signals to the sample, including those used to determine the presence and/or concentration of the analyte and those used to determine other factors, such as the hematocrit content of the sample or the fill state of the test sensor.

In addition to the first input signal application 1340, an initial polling potential may be input before the first input signal application 1340 to determine the presence of the sample. A potential also may be applied between any pair of electrodes and/or conductors to remove material from the electrode and/or conductor surface, to alter the chemistry of an electrode, or to oxidize or reduce a portion of the charge transfer system. Such a potential may be applied before the analysis.

In the second input signal application 1350 of FIG. 13, the system applies a second input signal at a different potential to the sample using a second counter electrode. The ability to select the working potential of multiple working electrodes and/or the ability to select the operating potential of multiple counter electrodes provides the biosensor system with the ability to perform multiple types of analysis. During an analysis, the potential between any pair of multiple working, counter, and/or reference electrodes may be measured to provide useful information. By providing the sample reservoir with multiple sequentially filled secondary analysis regions, the progress of reservoir filling by the sample may be monitored using the two or more input signal applications 1340, 1350.

In sample determination 1360, the measurement device analyzes output signals responsive to the two input signals to determine the presence and/or concentration of at least one measurable species in the sample at each potential. If the oxidoreductase or similar species used in the redox reaction 1320 reacts with a single analyte, specificity may be provided to a portion of the generated electrical signal. As more than one measurable species may be ionized by different portions of the input signal, the presence, and/or concentration of multiple analytes, mediators, interferents, and the like may be determined. Additional current, time, and/or other values also may be analyzed. For example, the currents determined for one analyte, mediator, or interferent may be modified with the currents determined for another analyte, mediator, or interferent to increase the measurement performance of the system.

Gated input signals, such as gated amperometric, gated voltammetric, and/or combinations thereof, may be used to address the potential of a specific mediator and solve the linear equation set. When a test sensor having electrically independent counter electrodes and electrically connected working electrodes is used, for example, the concentrations of three different measurable species may be determined by solving equations (1) through (3):

$$i_{low} = A_1 * S_1 + \text{Int}_1, \tag{1}$$

$$i_{medium} = i_{low} + i_2 = k_1 * (A_1 * S_1 + \text{Int}_1) + k_2 * (A_2 * S_2 + \text{Int}_2), \tag{2}$$

$$I_{high} = i_{medium} + i_3 = k_1 * (A_1 * S_1 + \text{Int}_1) + k_2 * (A_2 * S_2 + \text{Int}_2) + k_3 * (A_3 * S_3 + \text{Int}_3) \tag{3}$$

where $i_{low}$, $i_{medium}$ and $i_{high}$ are currents from coupling with counter electrodes of low, medium and high potentials; $A_1$, $A_2$ and $A_3$ are the concentrations of the three different measurable species; $k_1$, $k_2$ and $k_3$ are proportionality constants that express the current difference between two of the operating potentials; and S and Int are the slope and intercept for each analyte calibration system, respectively.

Figure 14A:
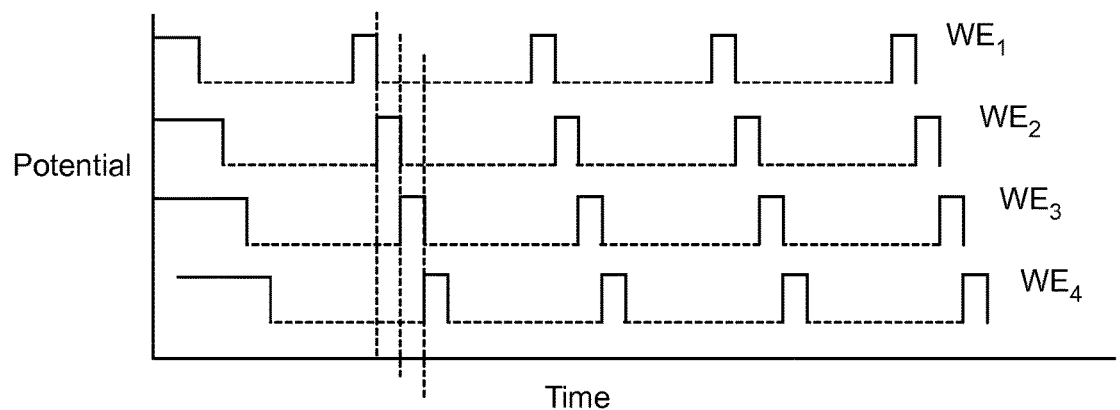
FIG. 14A represents the input signal from a sequential gated amperometric pulse sequence used in combination with a test sensor having independently addressable counter and working electrodes.
Figure 14B:
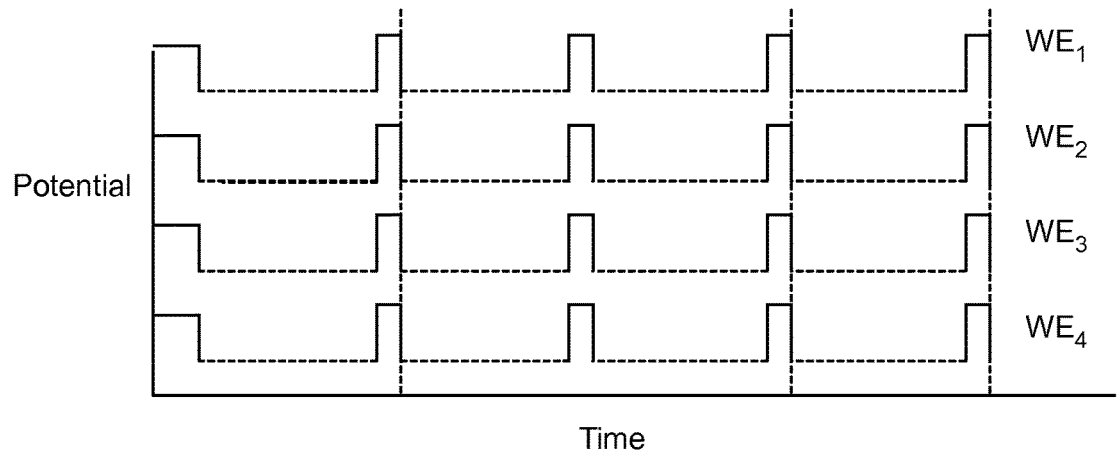
FIG. 14B represents the input signal from a simultaneous gated amperometric pulse sequence used in combination with a test sensor having independently addressable counter and working electrodes.

FIG. 14A represents the input signal from a sequential gated amperometric pulse sequence used in combination with a test sensor having independently addressable counter and working electrodes ($WE_1$-$WE_4$). In this instance, one working electrode operates at a time, and the input signal is sequentially input to each electrode pair. In this manner, a multi-potential potentiostat is not required to determine the output signal from multiple pairs of electrodes. FIG. 14B represents the input signal from a simultaneous gated amperometric pulse sequence used in combination with a test sensor having independently addressable counter and working electrodes ($WE_1$-$WE_4$). In this instance all four electrode pairs are simultaneously operated at the same potential for each excitation. While not shown in the figure, the input signal could be simultaneously applied to two or more of the electrodes while being sequentially applied to other electrodes.

By connecting multiple independently addressable counter electrodes to a current/voltage converter, the output currents resulting from the analysis may be measured separately. This operation may be combined with a gated input signal where one counter electrode is off, while a second counter electrode is on. The resulting cascade of measurement currents from independent counter electrodes provides a way to analyze multiple analytes and other components of the sample. Linear combinations of equations may be solved to determine the concentration and/or other parameters of individual analytes.

Applied input signals may have voltages from 0.05 to 1.0 V, preferably from 0.1 to 0.8 V, and more preferably from 0.2 to 0.5 V. The input signals may be provided over a duration of from 0.01 second to 3 minutes, depending on the analyte or analytes of interest. For example, a glucose analysis may be complete in less than 5 seconds while other analytes may benefit from longer duration input signals. If the input signal includes multiple excitations and relaxations, the duration of each excitation may be from 0.01 to 7 seconds, preferably from 0.5 to 3 seconds, and more preferably from 0.1 to 2 seconds for glucose, for example. Other input signal and excitation durations may be used.

In sample concentration transmission 1370 of FIG. 13, the measurement device converts at least one measurable species concentration into a sample analyte concentration and may display, store for future reference, further process, and/or use one or more of the determined measurable species concentrations for additional calculations. For example, the value determined for one analyte, mediator, or interferent may be modified with the value determined for another analyte, mediator, or interferent to increase the measurement performance of the system.

A counter electrode having an oxidizable species present in the charge transfer system also may be used as a working electrode lacking the oxidoreductase, thus providing the ability to analyze for hematocrit and determine the background component of the output signal. The analyte concentration may be modified with this and other information to increase accuracy and/or precision. A counter electrode may be used as a working electrode during an open circuit to measure one or more hematocrit parameters. In another aspect, one or more output signals may be correlated with a calibration curve or look-up table to determine hematocrit bias or bias attributable to an interferent.

Depending on the nature of the analyte, the concentration of one analyte may be used to alter the reading of another analyte. For example, when the concentration of a first analyte positively interferes with the concentration of a second analyte, the concentration of the first analyte may be subtracted from the concentration of the second analyte to increase the accuracy and/or precision of the concentration value determined for the second analyte.

Figure 15:
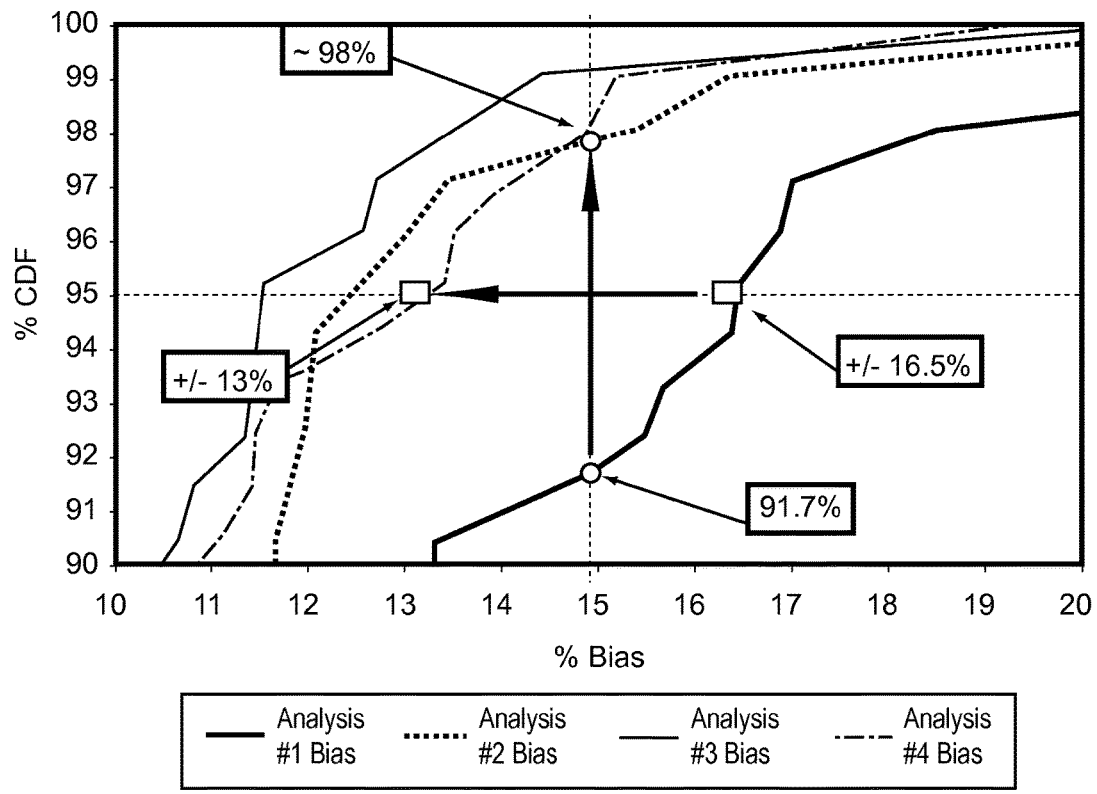
FIG. 15 shows the results of averaging the results of up to four separate analyses for the same analyte to determine the concentration of the analyte in the sample.

FIG. 15 shows the results of averaging the results of up to four separate analyses for the same analyte to determine the concentration of the analyte in the sample. As shown in the graph, by increasing the number of separate analysis performed from one to three, 98% of the obtained concentration values fell within ±15% bias limit when compared to a reference YSI instrument. While the data underlying the graph was obtained from separate test sensors, test sensors having two or more secondary analysis regions may be configured to perform the same analysis in more than one secondary region in addition to analyzing for different analytes. Thus, multiple substantially chemically isolated secondary analysis regions may provide the benefits of signal averaging from a single test sensor.

The ability to perform the same analysis multiple times on a single test sensor may significantly increase the accuracy and/or precision of the determined analyte concentration. Thus, signal averaging made possible by performing the same analysis multiple times on the same test sensor may provide an enhancement in the signal-to-noise ratio for the test sensor by reducing random noise (as characterized by the standard deviation sd value) at the rate of $1/\sqrt{n}$ in relation to conventional sensor systems.

Figure 16:
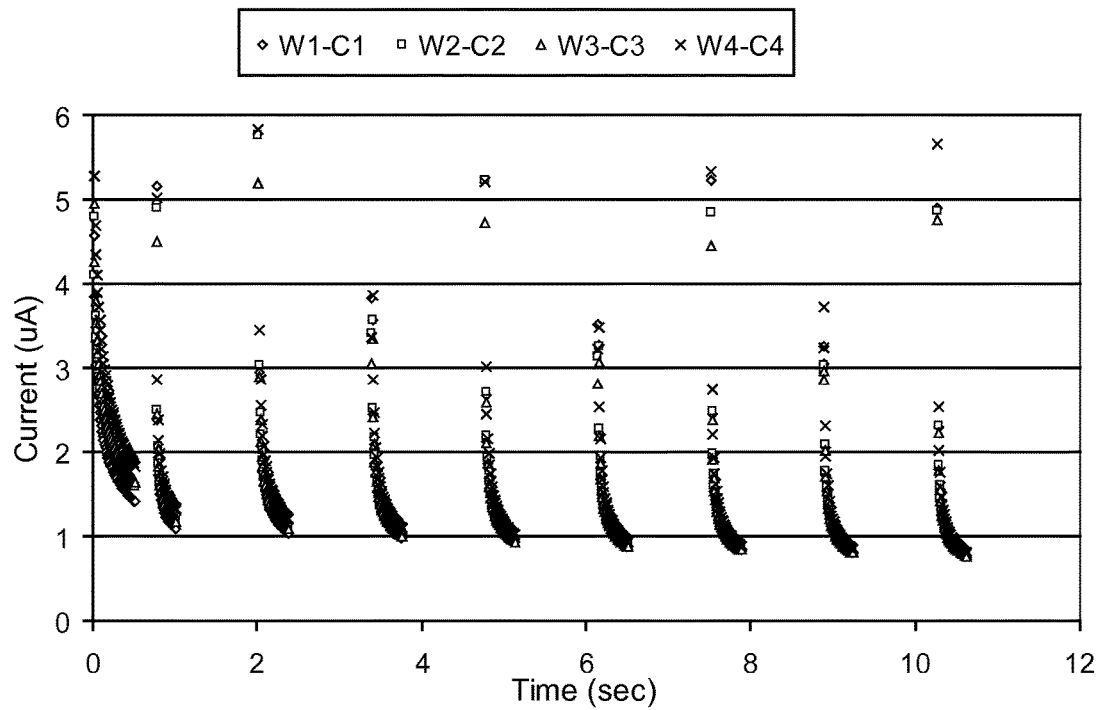
FIG. 16 depicts the current decays obtained from a signal averaging experiment.

FIG. 16 depicts the current decays obtained when a gated amperometric input signal is simultaneously applied to eight individually addressable and substantially chemically isolated electrodes. The electrodes were configured in a multi-T-design with four working electrodes opposing four counter electrodes across the primary channel, such as previously depicted in FIG. 3I. Each working electrode was formed with a reagent composition including 0.5% (w/w) HEC binder, 50 mL of the Structure I molecule, and 2 U/μL of the PQQ-GDH enzyme system in a phosphate buffer of pH 7. Each counter electrode was formed with a charge transfer system including 0.5% (w/w) HEC binder and substantially pure ferricyanide 100 mM in phosphate buffer of pH 7.

To conduct the experiment, a sample including 100 mg/dL of glucose in phosphate buffer of pH 7 was introduced to the test sensor and a gated amperometric input signal was simultaneously applied across each of the four opposing electrode pairs. The gated input signal included two initial excitations having varying pulse widths followed by seven excitations having a pulse width of 0.375 seconds. The latter seven excitations were separated by one second relaxation periods. Toward the end of the excitation applied at the two second time point, for example, the four current values corresponding to each electrode pair (W1-C1, W2-C2, W3-C3, and W4-C4) are averaged. From this average of four current values, an analyte concentration of the sample may be determined using one or more correlation equations or a similar method. In this manner, the previously discussed accuracy and/or precision benefits obtained from averaging multiple analyses may be obtained from a single test sensor.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:
1. An analyte test sensor, comprising:
    at least two substrates in the form of a base and a lid combined to form a reservoir, the reservoir having a primary area between eight secondary analysis regions, the eight secondary analysis regions including a first region, a second region, a third region, a fourth region, a fifth region, a sixth region, a seventh region, and an eight region, the eight secondary analysis regions being distinct, separate, and structurally isolated to resist or eliminate diffusive or convective mixing of reagents between the secondary analysis regions during one or more analyses of a sample, the primary area having a sample port where sample introduction occurs into the test sensor;

four working electrodes including a first working electrode, a second working electrode, a third working electrode, and a fourth working electrode, the four working electrodes being distinct and separate, each of the working electrodes including a first conductor and a reagent composition, each of the reagent compositions having a different redox potential; and four counter electrodes including a first counter electrode, a second counter electrode, a third counter electrode, and a fourth counter electrode, the four counter electrodes being distinct and separate, each of the counter electrodes including a second conductor and at least one redox species, wherein each of the four working electrodes and the four counter electrodes is disposed in a respective separate one of the eight secondary analysis regions such that the first region has the first working electrode and its respective first conductor and reagent composition, the second region has the second working electrode and its respective first conductor and reagent composition, the third region has the third working electrode and its respective first conductor and reagent composition, the fourth region has the fourth working electrode and its respective first conductor and reagent composition, the fifth region has the first counter electrode and its respective second conductor and at least one redox species, the sixth region has the second counter electrode and its respective second conductor and at least one redox species, the seventh region has the third counter electrode and its respective second conductor and at least one redox species, and the eighth region has the fourth counter electrode and its respective second conductor and at least one redox species;

wherein the first conductors of the working electrodes are electrically connected; and wherein the second conductors of the counter electrodes are not electrically connected.

2. The test sensor of claim 1, wherein at least one of the secondary analysis regions opposes another one of the second secondary analysis regions across the primary area.

3. The test sensor of claim 1, wherein at least two of the secondary analysis regions are staggered on opposing sides of the primary area.

4. The test sensor of claim 2, wherein at least two of the secondary analysis regions are staggered on opposing sides of the primary area.

5. The test sensor of claim 2, wherein at least one of the secondary analysis regions branch from the primary area at an angle other than 90°.

6. The test sensor of 3, wherein at least one of the secondary analysis regions branch from the primary area at an angle other than 90°.

7. The test sensor of claim 4, wherein at least one of the secondary analysis regions branch from the primary area at an angle other than 90°.

8. The test sensor of claim 2, wherein at least one of the secondary analysis regions branch from the primary area at an angle of less than 90°.

9. The test sensor of claim 3, wherein at least one of the secondary analysis regions branch from the primary area at an angle of less than 90°.

10. The test sensor of claim 4, wherein at least one of the secondary analysis regions branch from the primary area at an angle of less than 90°.

11. The test sensor of claim 1, wherein the four working electrodes are disposed in four of the secondary analysis regions on one side of the primary area, and the four counter electrodes are disposed in four other secondary analysis regions on another side of the primary area.

12. The test sensor of claim 1, further comprising another conductor connected to one of the counter electrodes and extending into the primary area.

13. The test sensor of claim 1, wherein the reservoir is a multi-T-channel design.

14. The test sensor of claim 1, wherein the reservoir is a multi-Y-channel design.

15. The test sensor of claim 1, wherein the counter electrodes are configured to operate at different potentials.

16. The test sensor of claim 1, wherein the counter electrodes are configured to operate at different potentials separated by at least 50 mV.

17. The test sensor of claim 1, wherein the sample is a biological fluid, and wherein the secondary analysis regions are arranged so that when the biological fluid enters the reservoir and flows to the secondary analysis regions, the biological fluid does not flow across more than one electrode to reach another electrode.

18. The test sensor of claim 10, wherein the sample is a biological fluid, and wherein the secondary analysis regions are arranged so that when the biological fluid enters the reservoir and flows to the secondary analysis regions, the biological fluid does not flow across more than one electrode to reach another electrode.

19. The test sensor of claim 1, wherein a single straight line drawn passing through the primary area and the secondary analysis regions cannot be drawn between any two electrodes.

20. The test sensor of claim 10, wherein a single straight line drawn passing through the primary area and the secondary analysis regions cannot be drawn between any two electrodes.

21. The test sensor of claim 1, wherein at least two of the counter electrodes are configured to operate at different potentials.

22. The test sensor of claim 10, wherein at least two of the counter electrodes are configured to operate at different potentials.

23. The test sensor of claim 21, wherein the different potentials are separated by at least 50 mV.

24. The test sensor of claim 22, wherein the different potentials are separated by at least 50 mV.

25. The test sensor of claim 21, wherein different redox species of the at least two counter electrodes are selected from the group consisting of a metal verses an electroactive organic molecule and the elemental identity of a metal.

26. The test sensor of claim 22, wherein different redox species of the at least two counter electrodes are selected from the group consisting of a metal verses an electroactive organic molecule and the elemental identity of a metal.

27. The test sensor of claim 21, wherein the different redox potential is provided by first and second redox species having different ratios of the conjugates of a redox pair.

28. The test sensor of claim 22, wherein the different potential configuration is provided by first and second redox species having different ratios of the conjugates of a redox pair.

29. The test sensor of claim 1, further comprising at least one reference electrode.

30. The test sensor of claim 10, further comprising at least one reference electrode.

31. An analyte test sensor, the test sensor comprising:
at least two substrates in the form of a base and a lid combined to form a reservoir, the reservoir including at least one primary area located between at least eight secondary analysis regions, the eight secondary analysis regions including a first region, a second region, a third region, a fourth region, a fifth region, a sixth region, a seventh region, and an eighth region, the eight secondary analysis regions being distinct, separate, and structurally isolated to resist or eliminate diffusive or convective mixing of reagents between the secondary analysis regions during one or more analyses of a sample;
four working electrodes and four counter electrodes including a first working electrode, a second working electrode, a third working electrode, a fourth working electrode, a first counter electrode, a second counter electrode, a third counter electrode, and a fourth counter electrode, each of the four working electrodes and the four counter electrodes being distinct and separate, each of the four working electrodes including a first conductor and a reagent composition, each of the reagent compositions having a different redox potential, each of the four counter electrodes including a second conductor and at least one redox species, the first conductors of the four working electrodes being electrically connected and the second conductors of the four counter electrodes not being electrically connected, each of the four working electrodes and the four counter electrodes being disposed in a respective separate one of the eight secondary analysis regions such that the first region has the first working electrode and its respective first conductor and reagent composition, the second region has the second working electrode and its respective first conductor and reagent composition, the third region has the third working electrode and its respective first conductor and reagent composition, the fourth region has the fourth working electrode and its respective first conductor and reagent composition, the fifth region has the first counter electrode and its respective second conductor and at least one redox species, the sixth region has the second counter electrode and its respective second conductor and at least one redox species, the seventh region has the third counter electrode and its respective second conductor and at least one redox species, and the eighth region has the fourth counter electrode and its respective second conductor and at least one redox species;
at least one sample port in fluid communication with the primary area, wherein the at least one sample port is where sample introduction occurs into the test sensor;
a first vent in fluid communication with the first region; and
a second vent in fluid communication with the second region.

32. An analyte test sensor, comprising:
at least two substrates in the form of a base and a lid combined to form a reservoir, the reservoir having a primary area between at least eight secondary analysis regions, the eight secondary analysis regions including a first region, a second region, a third region, a fourth region, a fifth region, a sixth region, a seventh region, and an eight region, the eight secondary analysis regions being distinct, separate, and structurally isolated to resist or eliminate diffusive or convective mixing of reagents between the secondary analysis regions during one or more analyses of a sample, the primary area having a sample port where sample introduction occurs into the test sensor;
four working electrodes and four counter electrodes including a first working electrode, a second working electrode, a third working electrode, a fourth working electrode, a first counter electrode, a second counter electrode, a third counter electrode, and a fourth counter electrode, each of the four working electrodes and the four counter electrodes being distinct and separate, each of the four working electrodes including a first conductor and a reagent composition, each of the reagent compositions having a different redox potential, each of the four counter electrodes including a second conductor and at least one redox species, the redox species of at least one counter electrode being different than the redox species of another counter electrode, the first conductors being electrically connected and the second conductors not being electrically connected;
wherein each of the four working electrodes and the four counter electrodes is disposed in a respective separate one of the eight secondary analysis regions such that the first region has the first working electrode and its respective first conductor and reagent composition, the second region has the second working electrode and its respective first conductor and reagent composition, the third region has the third working electrode and its respective first conductor and reagent composition, the fourth region has the fourth working electrode and its respective first conductor and reagent composition, the fifth region has the first counter electrode and its respective second conductor and at least one redox species, the sixth region has the second counter electrode and its respective second conductor and at least one redox species, the seventh region has the third counter electrode and its respective second conductor and at least one redox species, and the eighth region has the fourth counter electrode and its respective second conductor and at least one redox species;
where at least one of the conductors is disposed between the two substrates; and
wherein the sample port is defined at least by the two substrates and an edge of the conductor disposed between the two substrates, the edge of the conductor defining at least one of the working electrode and the counter electrode.

33. An analyte test sensor, comprising:
at least two substrates in the form of a base and a lid combined to form a reservoir, the reservoir including at least one primary area, at least one sample port, at least one vent, and at least eight secondary analysis regions, the eight secondary analysis regions including a first region, a second region, a third region, a fourth region, a fifth region, a sixth region, a seventh region, and an eight region, the eight secondary analysis regions being distinct, separate, and structurally isolated to resist or eliminate diffusive or convective mixing of reagents between the secondary analysis regions during one or more analyses of a sample;

four working electrodes and four counter electrodes including a first working electrode, a second working electrode, a third working electrode, a fourth working electrode, a first counter electrode, a second counter electrode, a third counter electrode, and a fourth counter electrode, each of the four working electrodes and the four counter electrodes being distinct and separate, each of the four working electrodes including a first conductor and a reagent composition, each of the reagent compositions having a different redox potential, each of the four counter electrodes including a second conductor and at least one redox species, the redox species of at least one counter electrode being different than the redox species of another counter electrode, the first conductors of the working electrodes being electrically connected, the second conductors of the counter electrodes not being electrically connected;

wherein each of the four working electrodes and the four counter electrodes is disposed in a respective separate one of the eight secondary analysis regions such that the first region has the first working electrode and its respective first conductor and reagent composition, the second region has the second working electrode and its respective first conductor and reagent composition, the third region has the third working electrode and its respective first conductor and reagent composition, the fourth region has the fourth working electrode and its respective first conductor and reagent composition, the fifth region has the first counter electrode and its respective second conductor and at least one redox species, the sixth region has the second counter electrode and its respective second conductor and at least one redox species, the seventh region has the third counter electrode and its respective second conductor and at least one redox species, and the eighth region has the fourth counter electrode and its respective second conductor and at least one redox species;

wherein the structural isolation of the secondary analysis regions is achieved by at least one of: (a) a cross-sectional area of an entrance to each of the eight secondary analysis regions, (b) a distance between any two electrodes within each of the eight secondary analysis regions, or (c) a physical arrangement of each of the eight secondary analysis regions in relation to each other and in relation to the primary area, wherein the at least one sample port is where sample introduction occurs into the test sensor; and wherein a fluid sample entering the at least one sample port does not flow across more than one electrode of the four working electrodes and the four counter electrodes to reach another electrode of the four working electrodes and the four counter electrodes.

34. An analyte test sensor, comprising;

at least two substrates in the form of a base and a lid combined to form a reservoir, the reservoir including at least one primary area and at least eight secondary analysis regions, the eight secondary analysis regions including a first region, a second region, a third region, a fourth region, a fifth region, a sixth region, a seventh region, and an eight region, the eight secondary analysis regions being distinct, separate, and structurally isolated such that chemical analysis of reagents is different in each of the secondary analysis regions during one or more analyses of a sample, the primary area having a sample port where sample introduction occurs into the test sensor;

four working electrodes and four counter electrodes including a first working electrode, a second working electrode, a third working electrode, a fourth working electrode, a first counter electrode, a second counter electrode, a third counter electrode, and a fourth counter electrode, each of the four working electrodes and the four counter electrodes being distinct and separate, each of the four working electrodes including a first conductor and a reagent composition, each of the reagent compositions having a different redox potential, each of the four counter electrodes including a second conductor and at least one redox species, the first conductors being electrically connected, the second conductors not being electrically connected;

wherein each of the four working electrodes and the four counter electrodes is disposed in a respective separate one of the eight secondary analysis regions such that the first region has the first working electrode and its respective first conductor and reagent composition, the second region has the second working electrode and its respective first conductor and reagent composition, the third region has the third working electrode and its respective first conductor and reagent composition, the fourth region has the fourth working electrode and its respective first conductor and reagent composition, the fifth region has the first counter electrode and its respective second conductor and at least one redox species, the sixth region has the second counter electrode and its respective second conductor and at least one redox species, the seventh region has the third counter electrode and its respective second conductor and at least one redox species, and the eighth region has the fourth counter electrode and its respective second conductor and at least one redox species;

wherein a first redox species in electrical communication with the second conductor of the first counter electrode is different than a second redox species in electrical communication with the second conductor of the second counter electrode;

wherein when a sample consists essentially of a pH 7 phosphate buffer, 0.1 M sodium phosphate, and 16% (w/w) polyvinyl pyrrolidone polymer having a weight average molecular weight of 2000 that is introduced to the first and the second secondary analysis regions at an atmospheric relative humidity of 45° I and at a temperature of 22° C., mixing of the first and the second redox species is not observed by an analysis technique selected from the group consisting of cyclic voltammetry and chemoamperometry within 12 minutes if the test sensor is not mechanically disturbed.

35. An analyte biosensor system, comprising:

at least two substrates in the form of a base and a lid combined to form a reservoir, the reservoir including at least one primary area, at least one sample port, at least two vents, and at least eight secondary analysis regions, the eight secondary analysis regions including a first region, a second region, a third region, a fourth region, a fifth region, a sixth region, a seventh region, and an eight region, the eight secondary analysis regions being distinct, separate, and structurally isolated such that chemical analysis of reagents is different in each of the secondary analysis regions during one or more analyses of a sample, the at least one sample port being where sample introduction occurs into the test sensor;

four working electrodes and four counter electrodes including a first working electrode, a second working electrode, a third working electrode, a fourth working electrode, a first counter electrode, a second counter electrode, a third counter electrode, and a fourth counter electrode, each of the four working electrodes and the four counter electrodes being distinct and separate, each of the four working electrodes including a first conductor and a reagent composition, each of the reagent compositions having a different redox potential, each of the four counter electrodes including a second conductor and at least one redox species, the redox species of at least one counter electrode being different than the redox species of another counter electrode, the first conductors being electrically connected, the second conductors not being electrically connected, each of the four working electrodes and the four counter electrodes being disposed in a respective separate one of the eight secondary analysis regions such that the first region has the first working electrode and its respective first conductor and reagent composition, the second region has the second working electrode and its respective first conductor and reagent composition, the third region has the third working electrode and its respective first conductor and reagent composition, the fourth region has the fourth working electrode and its respective first conductor and reagent composition, the fifth region has the first counter electrode and its respective second conductor and at least one redox species, the sixth region has the second counter electrode and its respective second conductor and at least one redox species, the seventh region has the third counter electrode and its respective second conductor and at least one redox species, and the eighth region has the fourth counter electrode and its respective second conductor and at least one redox species;

a sample interface in electrical communication with the conductors in the reservoir;

a sensor interface in electrical communication with the sample interface; and a processor in electrical communication with the sensor interface, the processor being operable to determine the time when a fluid sample enters the reservoir and contacts the first working electrode, the processor being further operable to determine the time when a fluid sample enters the sample reservoir and contacts the first counter electrode;

wherein the structural isolation of the eight secondary analysis regions is achieved by at least one of (a) a cross-sectional area of an entrance to each of the eight secondary analysis regions, (b) a distance between any two electrodes within each of the eight secondary analysis regions, or (c) a physical arrangement of each of the eight secondary analysis regions in relation to each other and in relation to the primary area.

36. An analyte biosensor system, comprising:

a test sensor including a sample interface disposed on a first substrate in the form of a base, the sample interface being in electrical communication with a reservoir formed by combining the first substrate and a second substrate in the form of a lid, the reservoir having a primary area with at least one sample port and at least eight secondary analysis regions, the eight secondary analysis regions including a first region, a second region, a third region, a fourth region, a fifth region, a sixth region, a seventh region, and an eight region, the eight secondary analysis regions being distinct, separate, and structurally isolated such that chemical analysis of diffusive or convective mixing of reagents is different in each of the secondary analysis regions during one or more analyses of a sample, the at least one sample port being where sample introduction occurs into the test sensor;

four working electrodes and four counter electrodes including a first working electrode, a second working electrode, a third working electrode, a fourth working electrode, a first counter electrode, a second counter electrode, a third counter electrode, and a fourth counter electrode, each of the four working electrodes and the four counter electrodes being distinct and separate, each of the four working electrodes including a first conductor and a reagent composition, each of the reagent compositions having a different redox potential, each of the four counter electrodes including a second conductor and at least one redox species, the redox species of at least one counter electrode being different than the redox species of another counter electrode, the first conductors of the four working electrodes being electrically connected, the second conductors of the four counter electrodes not being electrically connected, each of the four working electrodes and the four counter electrodes being disposed in a respective separate one of the eight secondary analysis regions such that the first region has the first working electrode and its respective first conductor and reagent composition, the second region has the second working electrode and its respective first conductor and reagent composition, the third region has the third working electrode and its respective first conductor and reagent composition, the fourth region has the fourth working electrode and its respective first conductor and reagent composition, the fifth region has the first counter electrode and its respective second conductor and at least one redox species, the sixth region has the second counter electrode and its respective second conductor and at least one redox species, the seventh region has the third counter electrode and its respective second conductor and at least one redox species, and the eighth region has the fourth counter electrode and its respective second conductor and at least one redox species;

a sample interface in electrical communication with each of the first conductors and the second conductors in the reservoir; and a measurement device including a computer readable storage medium, a processor, and a signal generator, where the signal generator is in electrical communication with the sensor interface, and where the sensor interface is in electrical communication with the sample interface;

wherein the processor is operable to apply a first input signal at a first potential from the signal generator to at least one of the four working electrodes and at least a first counter electrode of the four counter electrodes, apply a second input signal at a second potential from the signal generator to at least one of the four working electrodes and at least a second counter electrode of the four counter electrodes, measure a first output signal from at least one of the four working electrodes and the first counter electrode, the first output signal being responsive to the first input signal, measure a second output signal from at least one of the four working electrodes and the second counter electrode the second output signal being responsive to the second input signal, analyze the first and the second output signals, determine a first concentration of at least one first measurable species in a biological sample disposed in the reservoir at the potential of the first input signal, determine a second concentration of at least one second measurable species in the biological sample disposed in the reservoir at the potential of the second input signal, and convert at least one of the first and the second concentrations into a concentration of the analyte in the biological sample disposed in the reservoir.

\* \* \* \* \*